US011992353B2

(12) United States Patent
Vaz et al.

(10) Patent No.: US 11,992,353 B2
(45) Date of Patent: May 28, 2024

(54) METHODS AND SYSTEMS FOR AN ADAPTIVE MULTI-PHASE ANGIOGRAPHY SCAN

(71) Applicant: GE Precision Healthcare LLC, Milwaukee, WI (US)

(72) Inventors: Michael Sarju Vaz, Milwaukee, WI (US); Chelsey Lewis, Waukesha, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 537 days.

(21) Appl. No.: 17/010,484

(22) Filed: Sep. 2, 2020

(65) Prior Publication Data
US 2022/0061791 A1  Mar. 3, 2022

(51) Int. Cl.
A61B 5/15        (2006.01)
A61B 6/00        (2006.01)
A61B 6/03        (2006.01)
A61B 6/50        (2024.01)
A61M 5/00        (2006.01)

(52) U.S. Cl.
CPC .............. A61B 6/504 (2013.01); A61B 6/032 (2013.01); A61B 6/481 (2013.01); A61B 6/542 (2013.01); A61M 5/007 (2013.01)

(58) Field of Classification Search
CPC ......... A61B 6/032; A61B 6/481; A61B 6/504; A61B 6/507; A61B 6/5217; A61B 6/542; A61M 5/007
See application file for complete search history.

(56) References Cited

U.S. PATENT DOCUMENTS

| 5,400,378 | A  | 3/1995  | Toth             |
|-----------|----|---------|------------------|
| 6,023,494 | A  | 2/2000  | Senzig et al.    |
| 6,236,706 | B1 | 5/2001  | Hsieh            |
| 6,256,368 | B1 | 7/2001  | Hsieh et al.     |
| 6,891,918 | B2 | 5/2005  | Drummond et al.  |
| 7,145,982 | B2 | 12/2006 | Ikeda et al.     |
| 7,983,460 | B2 | 7/2011  | Licato et al.    |
| 9,327,143 | B2 | 5/2016  | Gillece et al.   |
| 9,486,176 | B2 | 11/2016 | Goyal            |

(Continued)

FOREIGN PATENT DOCUMENTS

CN          101277648 A          10/2008

OTHER PUBLICATIONS

"The ONE Guides—4D Neurological Imaging," Cannon Medical Systems USA Website, Available Online at https://us.medical.canon/download/aq-one-club-guide-4d-neuro-imaging, Available Online at Early as Jan. 2010, 16 pages.

(Continued)

Primary Examiner — Mark D Remaly
(74) Attorney, Agent, or Firm — McCoy Russell LLP

(57) ABSTRACT

Methods and systems are provided for adaptive scan control. In one embodiment, a method includes processing acquired projection data of a monitoring area of a subject to measure a contrast signal of a contrast agent delivered to the subject, determining a hemodynamic marker of the subject based on the contrast signal, generating a scan prescription based on the determined hemodynamic marker of the subject, and performing a multi-phase contrast scan according to the scan prescription.

14 Claims, 17 Drawing Sheets

(56) References Cited

U.S. PATENT DOCUMENTS

| | | | |
|---|---|---|---|
| 9,517,042 | B2 | 12/2016 | Hsieh et al. |
| 9,622,717 | B2 | 4/2017 | Londt et al. |
| 10,349,909 | B2 | 7/2019 | Okerlund et al. |
| 2012/0121151 | A1* | 5/2012 | Bernhardt ............ A61B 6/481 382/131 |
| 2017/0086772 | A1 | 3/2017 | Vaz et al. |
| 2017/0209113 | A1 | 7/2017 | Jackson et al. |
| 2018/0049714 | A1 | 2/2018 | Nett |
| 2019/0231288 | A1 | 8/2019 | Profio et al. |

OTHER PUBLICATIONS

Hinzpeter, R. et al., "CT Angiography of the Aorta: Contrast Timing by Using a Fixed versus a Patient-specific Trigger Delay," University of Zurich Open Repository and Archive Website, Available Online at https://www.zora.uzh.ch/id/eprint/170529/1/radiol.2019182223.pdf, Available as Early as May 2019, 10 pages.

Lewis, C. et al., "Methods and Sytems for Protocol Management," U.S. Appl. No. 16/553,028, filed Aug. 27, 2019, 59 pages.

Vaz, M. et al., "Methods and Systems for Timing a Second Contrast Bolus," U.S. Appl. No. 16/672,261, filed Nov. 1, 2019, 84 pages.

Vaz, M. et al., "Methods and Systems for an Adaptive Multi-Phase Angiography Scan," U.S. Appl. No. 16/672,281, filed Nov. 1, 2019, 85 pages.

Vaz, M. et al., "Methods and Systems for an Adaptive Five-Zone Perfusion Scan," U.S. Appl. No. 16/672,314, filed Nov. 1, 2019, 85 pages.

Vaz, M. et al., "Methods and Systems for a Single-Bolus Angiography and Perfusion Scan," U.S. Appl. No. 16/672,336, filed Nov. 1, 2019, 85 pages.

Vaz, M. et al., "Methods and Systems for an Adaptive Four-Zone Perfusion Scan," U.S. Appl. No. 16/672,350, filed Nov. 1, 2019, 85 pages.

Vaz, M. et al., "Methods and Systems for an Adaptive Perfusion Scan," U.S. Appl. No. 16/698,291, filed Nov. 27, 2019, 43 pages.

* cited by examiner

|  | Marker Range<br>Marker =tSPt |  | # of Passes |
|---|---|---|---|
|  | marker ≤ | 20 s | 3 |
| 20s | < marker ≤ | 30s | 4 |
| 30s | < marker ≤ | 40s | 5 |
| 40s | < marker |  | 6 |

FIG. 12

|  | Marker Range<br>Marker = Time of x-ray on for pass #1 |  | Min # of passes | Max time between passes | Min time between 1st and last pass |
|---|---|---|---|---|---|
|  | marker ≤ | 20 s | 3 | 8 | 15 |
| 20 s | < marker ≤ | 30 s | 4 | 9 | 26 |
| 30 s | < marker ≤ | 40 s | 5 | 10 | 39 |
| 40 s | < marker |  | 6 | 11 | 54 |

METHODS AND SYSTEMS FOR AN ADAPTIVE MULTI-PHASE ANGIOGRAPHY SCAN

FIELD

Embodiments of the subject matter disclosed herein relate to non-invasive diagnostic imaging, and more particularly, to real-time adaptive contrast imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through a target volume, to acquire image data and to construct tomographic images (e.g., three-dimensional representations of the interior of the human body or of other imaged structures).

For emergency room (ER) stroke management, reducing an amount of time before a course of treatment is determined may increase favorable patient outcomes. For every minute a large vessel ischemic stroke is untreated, the average patient loses 1.9 million neurons. For each hour in which a treatment is ineffective, the patient loses as many neurons as it does in almost 3.6 years of normal aging. Current standards of care utilize a multi-phase CT angiography (CTA) scan that includes a head and neck CTA pass followed by two head only CTA passes that are spaced 8 seconds apart. If the patient is known to have atrial fibrillation or if the patient is over 80 years in age, then a fourth CTA pass may be acquired. For example, atrial fibrillation and 80 years in age are proxies for a long venous descent time back to baseline, and one goal of the mCTA is to acquire passes from an arterial peak though the end of the venous decent in order to access collateral blood flow to the infarcted area. Determining if there is collateral blood flow may help determine the course of treatment, for example. However, an emergency physician may have no prior knowledge (NPK) of the patient's hemodynamics, including whether the patient is known to have atrial fibrillation, or the patient's age.

BRIEF DESCRIPTION

This summary introduces concepts that are described in more detail in the detailed description. It should not be used to identify essential features of the claimed subject matter, nor to limit the scope of the claimed subject matter.

In one aspect, a method can include processing acquired projection data of a monitoring area of a subject to measure a contrast signal of a contrast agent delivered to the subject, determining a hemodynamic marker of the subject based on the contrast signal, generating a scan prescription based on the determined hemodynamic marker of the subject, and performing a multi-phase contrast scan according to the scan prescription.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 12 is a first example scan prescription lookup table that may be used in the method of FIG. 11;

FIG. 13 is a second example scan prescription lookup table that may be used in the method of FIG. 11;

DETAILED DESCRIPTION

Figure 1:
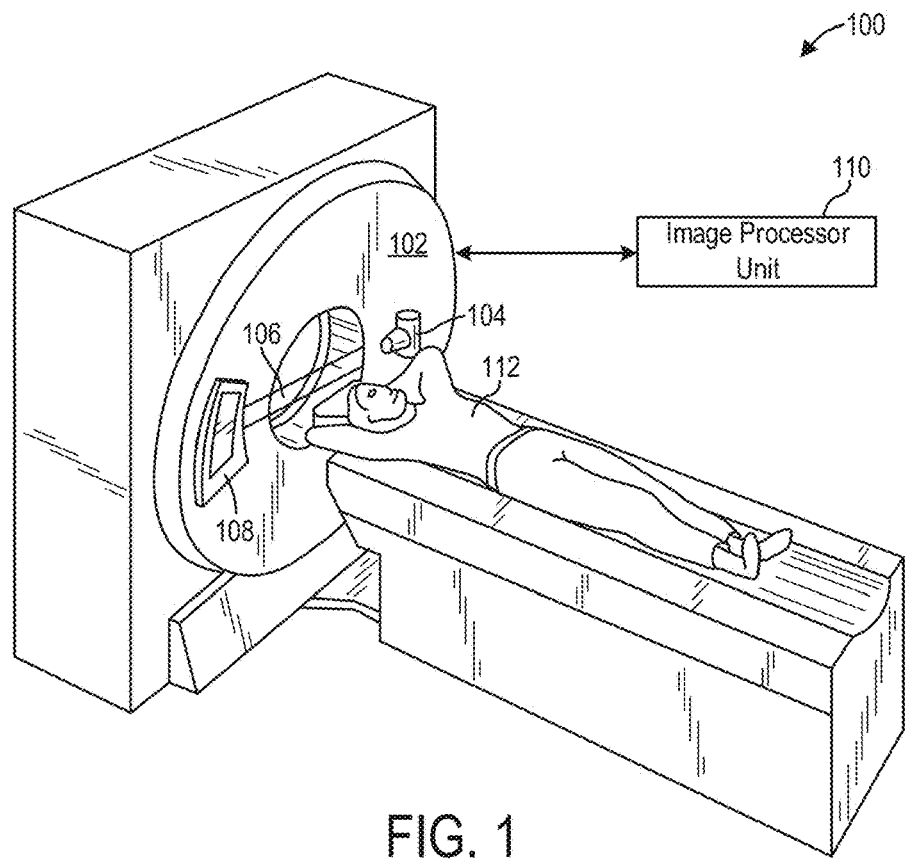
FIG. 1 shows a pictorial view of an imaging system, according to an embodiment.

Embodiments of the present disclosure will now be described, by way of example, with reference to the FIGS. 1-20, which relate to various embodiments for real-time adaptive contrast imaging. Contrast scans, when used during acute stroke care, may be used by clinicians as a tool to decide if a particular patient will benefit from endovascular thrombectomy. The contrast scans may include a computed tomography (CT) angiography (CTA) scan, for example. Due to the time sensitive nature of acute stroke care and the scan and reconstruction duration of a contrast scan, the contrast scan may be performed as soon as a patient arrives at a medical facility, often before patient information and any recent patient hemodynamic information is available, and the contrast scans may be performed as quickly as possible in order to expedite patient diagnosis. Due to differences in patient blood flow dynamics (e.g., hemodynamics) and age, an optimal number of contrast scan acquisitions and a timing of the acquisitions may vary from patient to patient. However, without recent patient hemodynamic information, contrast scans are typically performed according to fixed protocols that may be longer or shorter than necessary for a given patient. Further, the cognitive load placed on the scan machine operator/technologist during the time of the contrast scan may be relatively high, and any adaptations to predefined contrast scan protocols made on the fly as patient hemodynamic information is learned may further add to the cognitive load, thereby increasing the likelihood rescans may have to performed. For example, if the contrast scan is too short, such as when not enough acquisitions are performed and/or the acquisitions are spaced too closely together, the contrast scan may not provide enough information for a diagnosis to be made. If the contrast scan is too long, such as when unneeded acquisitions are performed and/or the acquisitions are spaced too far apart, a radiation dose provided to the patient may be increased and/or the scan may take additional time, thus prolonging an amount of time before the diagnosis can be made and delaying patient treatment.

Thus, according to embodiments disclosed herein, the number of acquisitions and the timing of the acquisitions may be determined automatically based on a hemodynamic marker that is estimated or directly measured from a contrast signal of a contrast agent injected into a patient. The contrast signal may be used to determine an arterial inflow function (AIF) curve, a venous outflow function (VOF) curve, and/or a tissue uptake curve (TUC), for example. The contrast agent injection may occur during a prior timing bolus or during a first acquisition of the contrast scan. The contrast signal may comprise a measured contrast level in a region of interest (e.g., an artery, such as the internal carotid artery) over a duration. Time points of interest, such as an arterial peak, a venous peak, and a venous return to baseline, may be determined from the contrast signal and used to determine the hemodynamic marker. As one example, the hemodynamic marker is an arterial peak time, comprising a duration between the arterial ascent knee time point and the arterial peak time point. The determined hemodynamic marker, which is specific to the patient being scanned, may be input into an adaptive contrast scan protocol, which may output an adaptive contrast scan prescription including the number of acquisitions and the timing of the acquisitions to use for the given value of the hemodynamic marker. As an example, the adaptive contrast scan protocol may include one or more lookup tables that relate a plurality of timing ranges for the hemodynamic marker to the number of acquisitions and timing of the acquisitions to use when the hemodynamic marker is within the given range. In some examples, the one or more lookup tables may trim acquisitions and/or adjust the timing of the acquisitions from a pre-determined fallback prescription, which is used when the hemodynamic marker cannot be determined or updates to the adaptive scan prescription cannot be made via the adaptive contrast scan protocol.

Further, both the fallback prescription and the adaptive contrast scan protocol may be defined by a lead technician/protocol manager ahead of time (e.g., not concurrent with performing a diagnostic scan of a patient) via an adaptive scan protocol graphical user interface (GUI). The adaptive scan protocol GUI may enable the lead technician/protocol manager to input preset scan parameters for a selected adaptive contrast scan protocol. To execute an adaptive contrast scan protocol to image a patient with an imaging system (e.g., a CT system), the operator/technologist of the imaging system may select the appropriate predefined adaptive contrast scan protocol. The predefined adaptive contrast scan protocol may be displayed to the operator via a run-time GUI, allowing the operator to confirm or, if necessary, change the preset scan parameters. The adaptive contrast scan prescription may be determined for carrying out the contrast scan based on the selected adaptive contrast scan protocol, any changes made to the preset scan parameters, and the determined hemodynamic marker of the patient (e.g., determined from the contrast signal measured from the patient at the region of interest). Thus, the adaptive contrast scan prescription may be adjusted as the contrast scan progresses based on the patient information that is collected during the scan. The progress of the scan may be displayed via the run-time GUI, including (at least in some examples) a visual representation of the adaptive contrast scan prescription.

In this way, a patient x-ray radiation dose may be reduced and/or a scan duration may be shortened while still acquiring high quality diagnostic images to support patient diagnosis. As a result, a likelihood that the images reconstructed from scan data acquired during the contrast scan will be non-diagnostic is reduced. Further, a number of tasks for the operator to perform is reduced while also increasing image quality consistency between operators and between patients.

Figure 2:
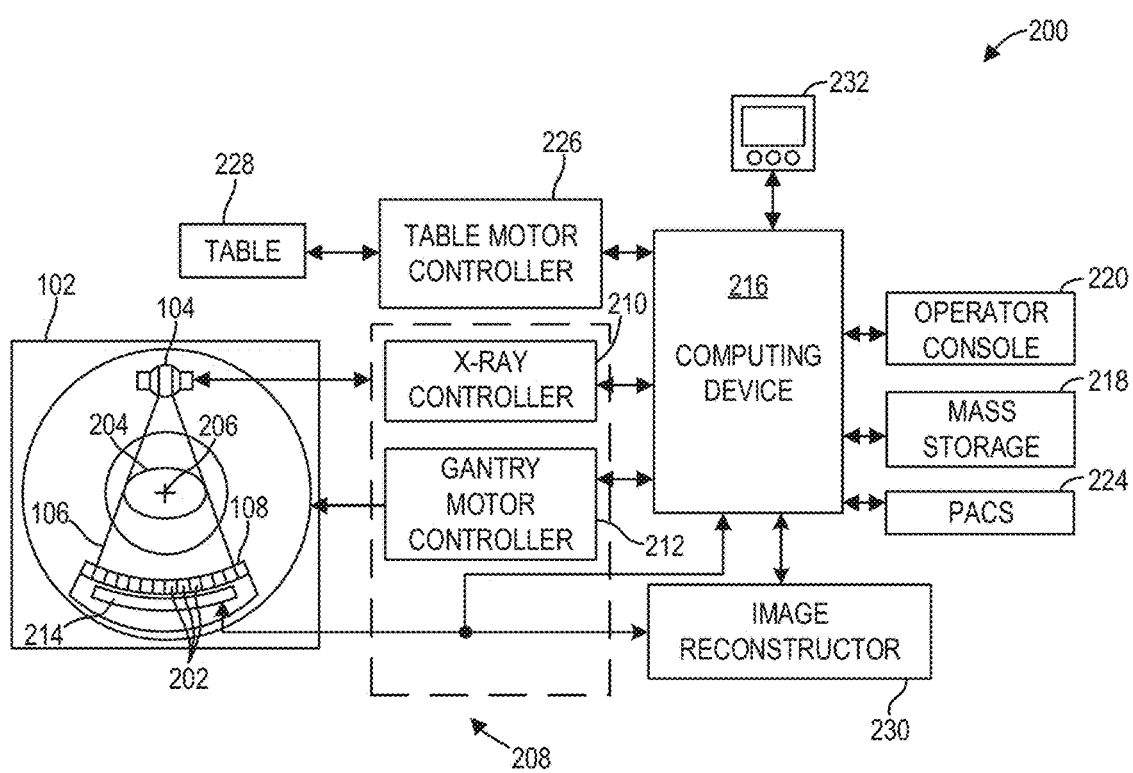
FIG. 2 shows a block schematic diagram of an exemplary imaging system, according to an embodiment.
Figure 3:
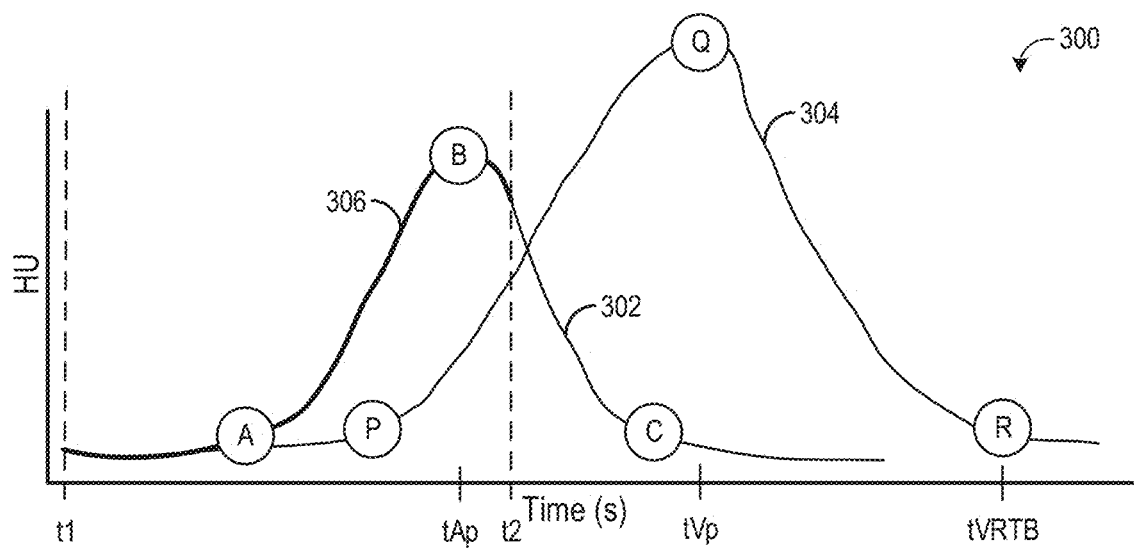
FIG. 3 shows a graph illustrating an example arterial inflow function (AIF) curve and an example a venous outflow function (VOF) curve generated during a contrast scan.
Figure 4:
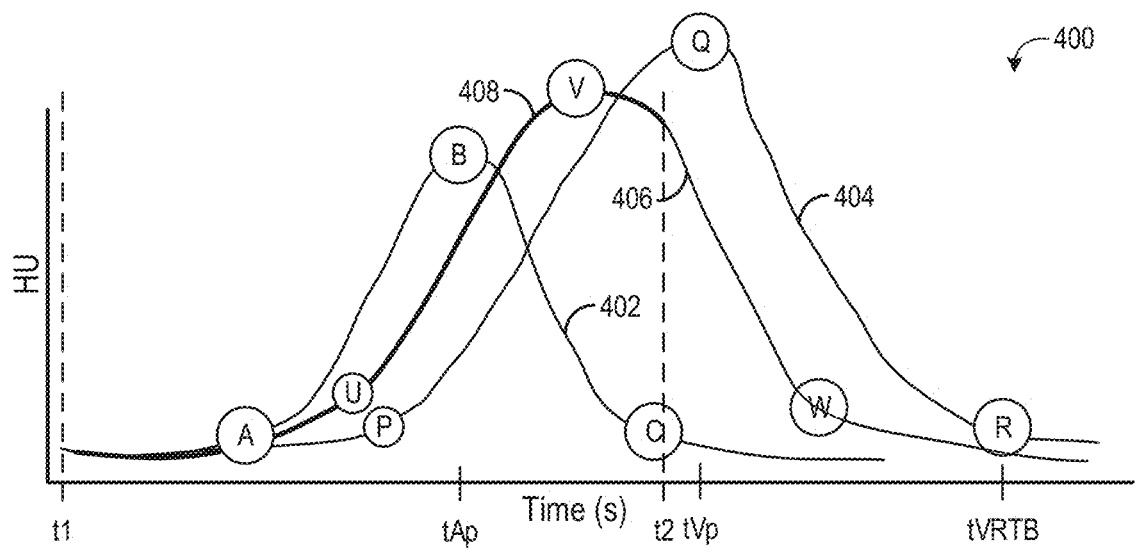
FIG. 4 shows a graph illustrating an example AIF curve, an example VOF curve, and an example tissue uptake curve (TUC) generated during a contrast scan.
Figure 14:
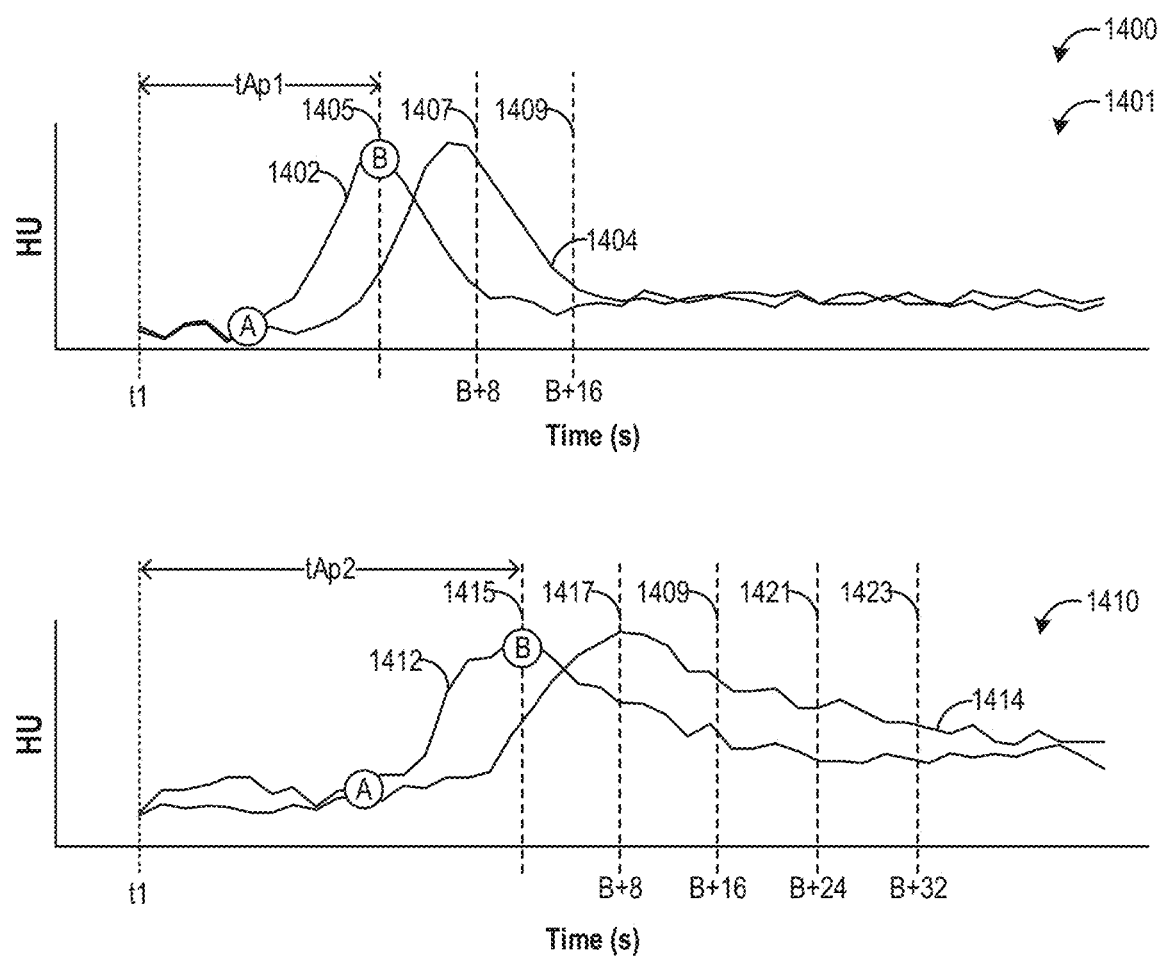
FIG. 14 shows plots of AIF and VOF curves and acquisition timings for two example patients, determined according to the method of FIG. 11.
Figure 18:
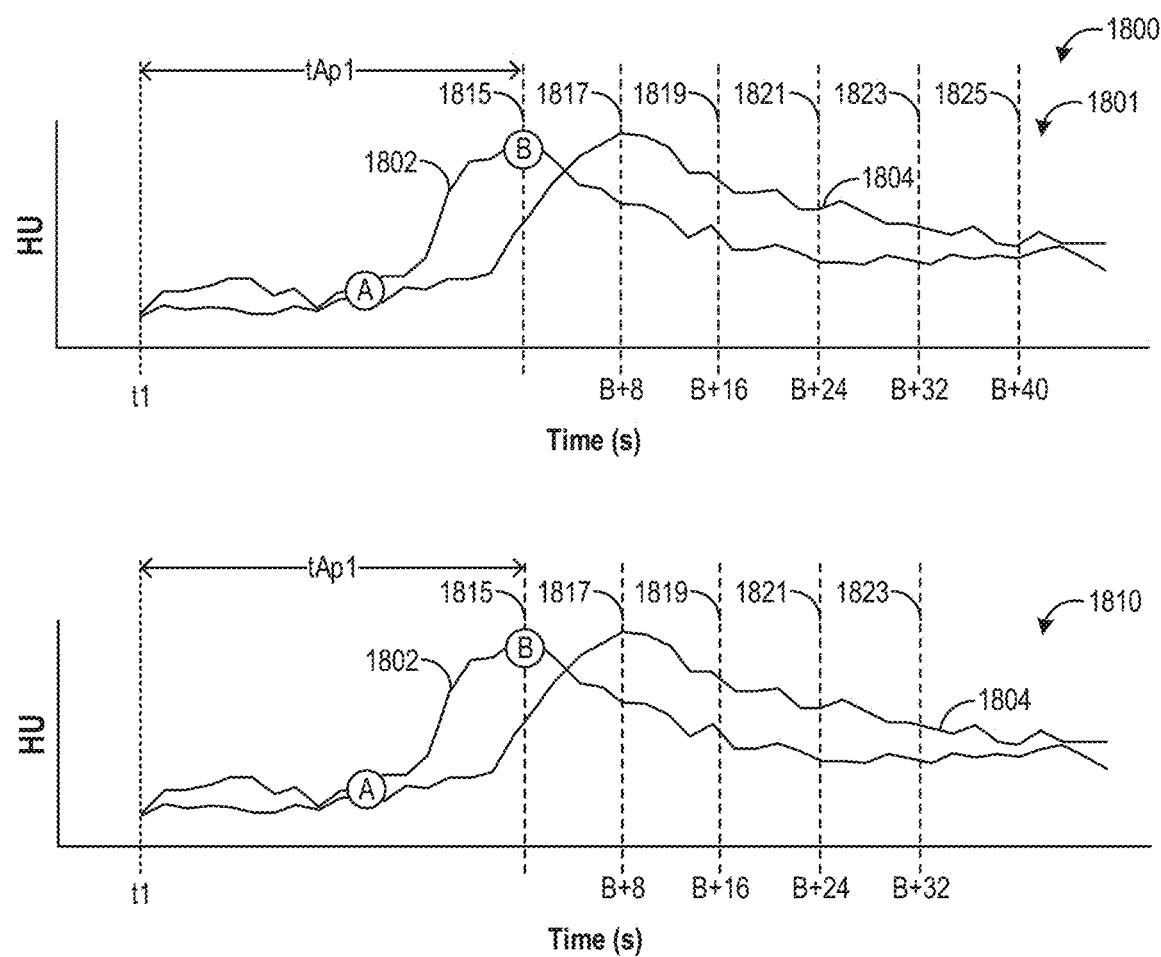
FIG. 18 is a set of graphs comparing angiography scan acquisitions and timings obtained according to a fallback scan prescription or an adaptive scan prescription for a first example patient, determined according to the workflow of FIG. 15.
Figure 19:
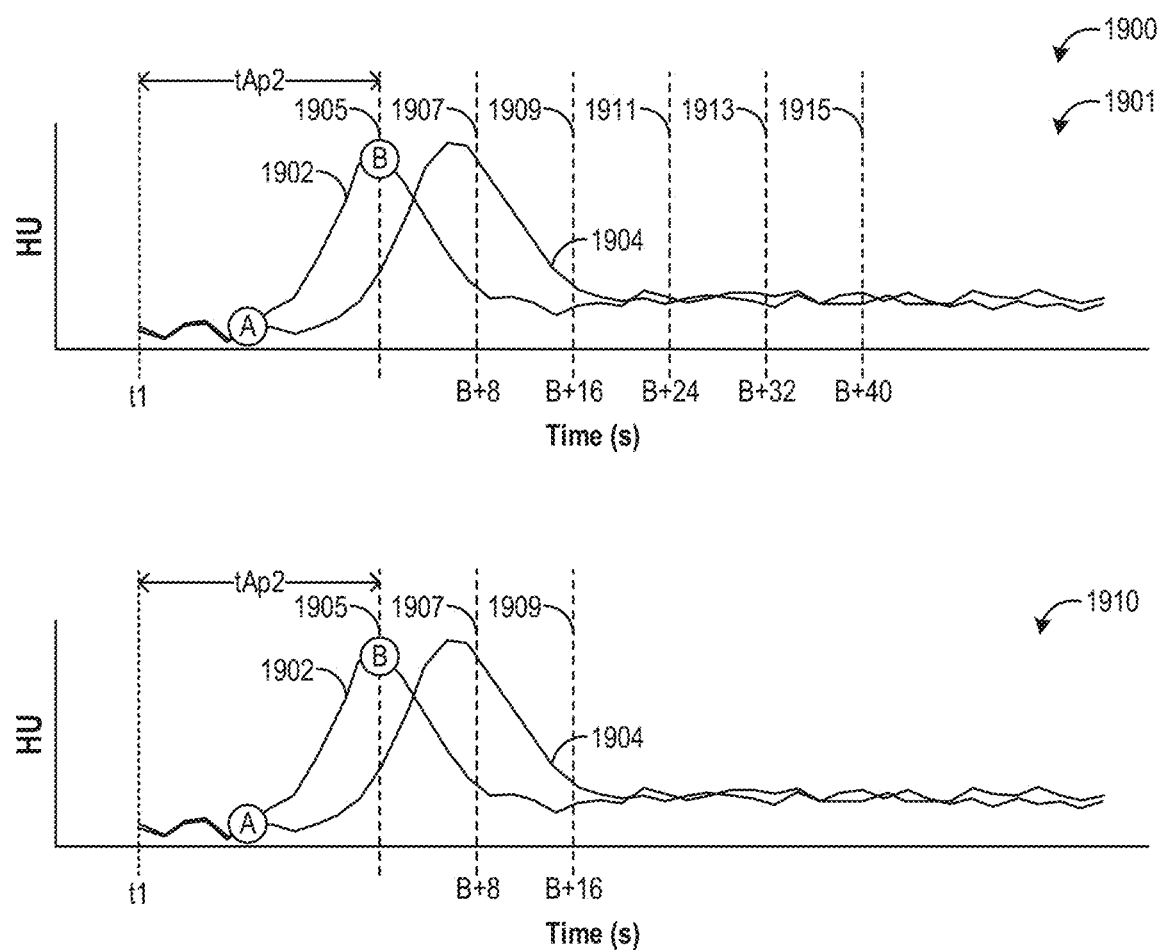
FIG. 19 is a set of graphs comparing angiography scan acquisitions and timings obtained according to a fallback scan prescription or an adaptive scan prescription for a second example patient, determined according to the workflow of FIG. 15.
Figure 20:
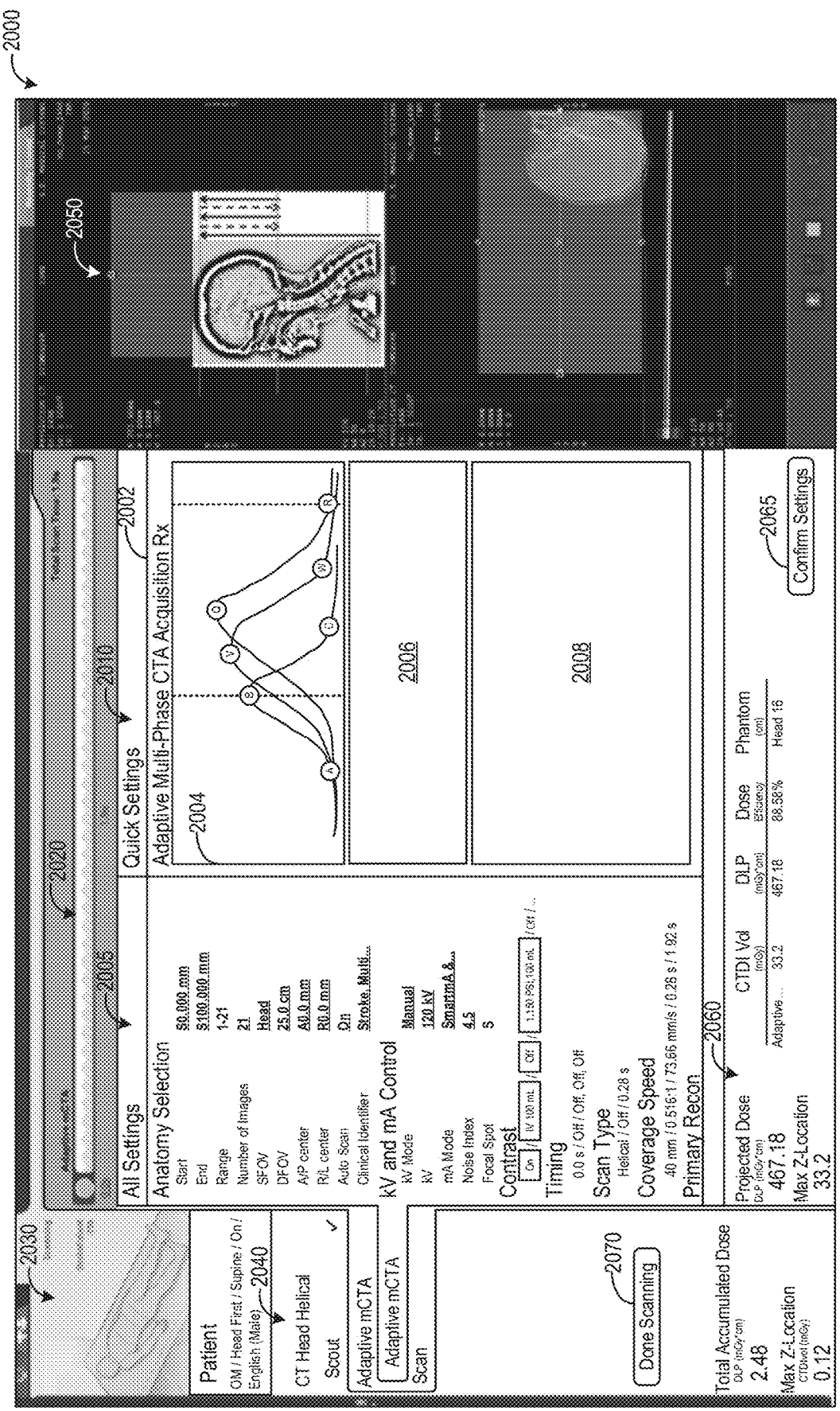
FIG. 20 shows an example of an adaptive scan run-time GUI, according to an embodiment.

An example of a computed tomography (CT) imaging system that may be used to perform contrast scans in accordance with the present techniques is provided in FIGS. 1 and 2. As described above, the timing of the contrast scans may be dependent on a hemodynamic marker determined from an AIF curve, a VOF curve, or a TUC of the contrast agent, which vary from patient to patient. FIG. 3 shows example AIF and VOF curves for a patient. At least a portion of the AIF curve may be directly measured prior to a first contrast scan commencing or during the first portion of the first contrast scan, and this portion may be used to determine the hemodynamic marker of the patient. As another example, rather than measuring the AIF, tissue uptake of the contrast agent may be measured, as shown in FIG. 4, and at least a measured portion of the TUC may be used to determine the hemodynamic marker. One or more adaptive contrast scan protocols may be defined in advance via an adaptive contrast scan GUI, such according to the method shown in FIG. 5 and via the example GUIs shown in FIGS. 6-10. During execution of a selected adaptive contrast scan protocol, the contrast scan may be carried out according to the method of FIG. 11. The adaptive contrast scan protocol may utilize one or more adaptive scan prescription lookup tables, such as the example lookup tables shown in FIGS. 12, 13, 16, and 17, in order to determine a number of acquisition phases and a timing of the acquisition phases for the hemodynamic marker of the patient being scanned. FIG. 14 shows a timeline of CT scan acquisitions and estimated AIF and VOF curves for two patients carried out according to the method of FIG. 11. Further, the adaptive contrast scan protocol may employ a workflow for updating the scan prescription from a fallback prescription in-flight, such as the example workflow shown in FIG. 15. FIGS. 18 and 19 show timelines of CT scan acquisitions and estimated AIF and VOF curves for two patients using according to the method of FIG. 11 and the workflow of FIG. 15. An example run-time GUI that may be displayed during the execution of the method of FIG. 11 is shown in FIG. 20.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality. Further, while the present techniques may be discussed herein with respect to head/neck scans such as acute stroke scan protocols, the present techniques may be applied during other contrast scan protocols, such as cardiac scans.

FIG. 1 illustrates an exemplary CT system 100 configured for CT imaging. Particularly, the CT system 100 is configured to image a subject 112, such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detector elements are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, e.g., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, a positron emission tomography (PET), or a single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods, such as maximum likelihood expectation maximization (MLEM) and ordered-subsets expectation-reconstruction techniques, as well as iterative reconstruction techniques. This process converts the attenuation measurements from a scan into integers called "CT numbers" or "Hounsfield units" (HU), which are used to control the brightness of a corresponding pixel on a display device.

To reduce the total scan time, a "helical" scan may be performed. To perform a "helical" scan, the patient is moved while the data for the prescribed number of slices are acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image are generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray beams 106 (see FIG. 1) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician may consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which, in turn, may control a table 228 which may be a motorized table. Specifically, the table motor controller 226 may move the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200, and instead, the computing device 216 may perform one or more functions of the image reconstructor 230. Moreover, the image reconstructor 230 may be located locally or remotely and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes described further herein (such as the methods described below with reference to FIGS. 5 and 11 and the workflow described with respect to FIG. 15) may be stored as executable instructions in non-transitory memory on a computing device (or controller) in the imaging system 200. In an embodiment, the computing device 216 may include the instructions in non-transitory memory, and may apply the methods described herein, at least in part, to determine a hemodynamic marker, which serves as a standard of comparison between patients, from a plurality of reconstructed images after receiving the reconstructed images from the image reconstructor 230. For example, the hemodynamic marker (also referred to herein as simply a "marker" or a "patient-specific marker") provides a measureable time event that relates to the flow of blood within organs and tissues of the patient, such as the arterial peak time. The computing device 216 may use the marker in order plan personalized contrast scan prescriptions, as described below. In other embodiments, image reconstructor 230 may include such executable instructions in non-transitory memory, and may apply the methods described herein to adaptively plan and control contrast scans. In yet another embodiment, the methods and processes described herein may be distributed across image reconstructor 230 and computing device 216.

In one embodiment, the display device 232 allows the operator to evaluate the imaged anatomy, view measured and/or estimated AIF and VOF curves, trigger aspects of the contrast scans, and the like. The display device 232 may also allow the operator to select a region of interest (ROI) and/or request patient information, for example, via a graphical user interface (GUI) for a subsequent scan or processing, as will be elaborated herein.

FIG. 3 shows a graph 300 depicting an example AIF curve 302 and an example VOF curve 304, each plotted as HU as a function of time. AIF curve 302 represents a change in an arterial inflow of a contrast agent over time for a patient, and VOF curve 304 represents a change in a venous outflow of the contrast agent over time for the patient. The AIF curve 302 may be measured at an arterial ROI, such as anterior cerebral artery or internal carotid artery, and may include a measurement of signal intensity in the arterial ROI relative to a baseline intensity (e.g., in the arterial ROI prior to contrast injection). The VOF curve 304 may be measured at a venous ROI, such as the superior sagittal sinus, and may include a measurement of the signal intensity in the venous ROI relative to a baseline intensity (e.g., in the venous ROI prior to contrast injection). Each of the AIF curve 302 and the VOF curve 304 comprises a contrast signal.

The AIF curve 302 may include an arterial ascent knee at approximately point A on the curve, an arterial peak at point B on the curve, and an arterial decent knee at approximately point C on the curve. An amount of time (e.g., time duration) from contrast injection at a time t1 until the arterial peak is reached may be the time to arterial peak, indicated as tAp on FIG. 3. The VOF curve 304 may include a venous ascent knee at approximately point P on the curve, a venous peak at point Q on the curve, and a venous decent knee at approximately point R on the curve. An amount of time from contrast injection until the venous peak is reached may be the time to venous peak, indicated as tVp on FIG. 3. An amount of time from contrast injection until the venous return to baseline (VRTB) is reached may be the time to VRTB, indicated as tVRTB on FIG. 3.

The amount of time it may take to reach the points marked on the curves in FIG. 3 may vary from patient to patient, as body weight, cardiac function, and other factors may impact the contrast agent inflow and outflow rate. As will be explained in more detail below, certain contrast scan protocols, such as angiography scans, rely on the AIF and/or VOF curves, and the timing of one or more of the points described above (e.g., the arterial peak) may be determined and used as a trigger for commencing diagnostic imaging, adjusting scan parameters, and the like. However, some scan protocols are condensed as much as possible so that diagnostic information may be learned as quickly as possible in order to facilitate patient care. For example, scan protocols carried out as part of an acute stroke assessment may be designed to be as short as possible while still collecting informative diagnostic image information so that a course of patient care may be determined and administered as quickly as possible. Thus, the amount of time it takes to accurately measure both the AIF curve and the VOF curve for a patient prior to initiation of the diagnostic scan(s) may delay patient care and negatively impact patient outcomes. Further, when the imaging system includes x-rays directed to the patient (such as the CT system described above with respect to FIGS. 1-2), it may be desired to minimize patient radiation exposure. Thus, acute stroke and other contrast scan protocols may include a short measurement of the AIF curve, for example, and scan protocol adjustments may be based on this limited information. Additionally or alternatively, certain aspects of the scan protocols may be carried out with fixed timing that is not changed from patient to patient. While such protocols may be suitable for ensuring that most scans generate sufficient diagnostic information, some scans may result in images that are not suitable for diagnosing the patient condition, may lead to unnecessary radiation exposure, or may result in treatment delays.

Thus, in some examples, prior to or during the beginning of a contrast scan, a first segment 306 of the AIF curve may be measured, and this AIF curve measurement (referred to as an AIF signal) may be used adjust (e.g., adapt) scan protocol parameters accordingly. Further, the scan protocol parameters may be adapted on the fly on a patient by patient basis and without prior knowledge of the patient age, cardiac function, etc. Further still, the scan protocol parameters may be adjusted without machine learning or other complex technologies.

In some embodiments, the first segment 306 of the AIF curve may be measured using a timing bolus (TB). The timing bolus may include a small amount of contrast agent that is administered before the contrast scan is initiated. The inflow of the contrast agent of the timing bolus may be monitored and used to set parameters for the following contrast scan. As shown, the first segment 306 of the AIF curve is measured as described above (e.g., in a ROI based on change in HU level relative to a baseline level). The first segment 306 may commence when the timing bolus is administered (e.g., at time t1 in FIG. 3) and end after the arterial peak (e.g., at time t2 in FIG. 3). As a result, time points A and B are measured via the timing bolus. In some examples, the first segment 306 may extend beyond what is shown in FIG. 3. For example, rather than terminating the measurement of the AIF curve at time t2, the measurement may extend until another suitable later time.

In another embodiment, the first segment 306 of the AIF curve may be measured using smart prep (SP). Smart prep may refer to an in-flight AIF measurement that occurs using the same contrast agent bolus that is administered for initiating the contrast scan. The inflow of the contrast agent of the contrast scan bolus may be monitored and used to set parameters for the in-flight contrast scan. For example, the smart prep may comprise a first pass of the mCTA, and the contrast agent inflow measured during the smart prep scan may trigger subsequent acquisition phase timings (e.g., a first exposure). Although the first segment 306 is shown in FIG. 3 as having the same beginning and ending timing whether the first segment 306 is measured using the timing bolus or using the smart prep, note that in other examples, the beginning and ending timing of the first segment 306 of the AIF curve that is used to adapt scan protocol parameters on the fly may vary between the methods. Either method may be used to determine the timing of time points A and B, but may differ in that the TB method uses a separate contrast agent injection and AIF curve measurement from the contrast scan while the SP method uses the same contrast agent injection and AIF curve measurement as the contrast scan.

While the TB and SP methods are both described above as being based on a single arterial ROI, it is to be understood that multiple arterial ROIs could be measured and combined (e.g., averaged) to measure the AIF curve. Further, the VOF curve could be measured for the same time period as the AIF curve (e.g., from time t1 until the time t2) by monitoring a venous ROI. The arterial ROI and the venous ROI described above may be positioned at any suitable location where arterial inflow and venous outflow, respectively, of contrast agent may be detectable, and the selection of where to position the arterial ROI and/or venous ROI may depend on the scan protocol (e.g., what anatomy is going to be imaged in the contrast scan). As an example, the scan protocol may include selection of an anatomy of interest from a plurality of possible anatomies of interest, including the head (e.g., the brain) and the liver.

As will be elaborated herein, the first segment 306 of the AIF curve may be used to determine a hemodynamic marker of the patient being imaged. For example, the hemodynamic marker may be the arterial peak time (tAp) corresponding to an amount of time between the contrast agent injection at time t1 and the peak of the AIF curve (point B). In such examples, the measured arterial peak time may be used to optimize a number of phases and or an amount of time between the phases of the contrast scan.

FIG. 4 shows a graph 400 depicting an example AIF curve 402, an example VOF curve 404, and an example tissue uptake curve (TUC) 406, each plotted as HU as a function of time. AIF curve 402 and VOF curve 404 may be the same as AIF curve 302 and VOF curve 304 described above with respect to FIG. 3. TUC 406 may represent a change in detected contrast agent in a tissue of interest, as the contrast agent is taken up by the tissue and then depleted from the tissue. To measure the TUC, the tissue of interest (e.g., the brain parenchyma) may be segmented in each of a plurality of reconstructed images, and the overall or average HU of in the segmented region of each of the plurality of reconstructed images may be determined relative to a baseline level and plotted over time. Thus, the TUC 406 may comprise a contrast signal.

The AIF curve 402 may include the time points discussed above (e.g., A, B, and C), and the VOF curve 404 may include the time points discussed above (e.g., P, Q, and R). The TUC 406 may include an ascent knee at approximately point U on the curve, a TUC peak at point V on the curve, and a decent knee at approximately point W on the curve. The timing of significant points is shown in FIG. 4, including tAp, tVp, and tVRTB.

In some embodiments, a segment of the TUC may be measured and then entered into a model to predict the AIF curve and the VOF curve, the remainder of the TUC, and/or time points of interest. As an example, the tissue uptake of a contrast agent (e.g., of a timing bolus) may be monitored and used to set parameters for the following contrast scan. As shown, a first segment 408 of the TUC is measured as described above (e.g., a change in HU level relative to a baseline level measured across a plurality of images). The first segment 408 may commence when the timing bolus is administered (e.g., at a time t1 in FIG. 4) and end after the TUC peak (e.g., at time t2 in FIG. 4). The first segment 408 may be entered into a model to estimate the remaining portion of the TUC 406 and all of the estimated AIF curve 402 and VOF curve 404. As a result, time points U and V are measured while time points A, B, C, P, Q, and R are estimated. For example, the TUC peak time is a duration between t1 and point V on the TUC 406. Thus, in some examples, the first segment 408 of the TUC may be measured and used to determine the time points A and B.

As explained above, a traditional multi-phase angiography contrast scan, referred as an mCTA, may include acquisitions during multiple phases of contrast agent enhancement/washout, such as a first phase that is typically performed at the arterial peak, a second phase that is performed at equilibrium or the venous peak, and a third phase that is performed during late venous/venous return to baseline. A typical head mCTA scan protocol may include a determination of when the arterial peak is to occur using the smart prep AIF measurement described above with respect to FIG. 3. A first acquisition is carried out at the estimated arterial peak, where the head and neck are imaged. Then, two additional acquisitions of the head only are carried out at fixed time points relative to the arterial peak, a second acquisition carried out at 8 seconds (or other suitable time) after the arterial peak and a third acquisition carried out at 16 seconds (or other suitable time) after the arterial peak.

Patients that are predicted to have a long venous phase, such as older patients (e.g., over 80) or patients with atrial fibrillation, may have mCTA scan protocols that dictate a fourth acquisition be performed at 24 seconds or other suitable time after the arterial peak.

However, these typical mCTA scan protocols may include the second, third, and/or fourth acquisitions being performed at times other than the target times, e.g., due to patient-to-patient variability in contrast enhancement and washout. Further, for patients with short arterial and/or venous phases, a fixed time mCTA scan may result in a scan that is longer than necessary, while for patients with relatively long venous phases (that are not older or have diagnosed atrial fibrillation), the fixed time mCTA scan may result in low quality diagnostic images if the final acquisition is performed before the venous return to baseline. Thus, according to embodiments disclosed herein, a personalized mCTA may be performed, where each acquisition of the mCTA is performed relative to the patient physiology (e.g., as determined from a measured or estimated AIF curves) and without prior knowledge (NPK) of the patient's physiology (e.g., the scan may be performed without relying on patient information or prior contrast scan information). For example, an AIF signal obtained according to the smart prep estimation method described above with respect to FIG. 3 may be used to trigger the first mCTA acquisition, and the measured tAp may be used to determining a timing and number of subsequent acquisition phases. In doing so, standardization in mCTA acquisitions may be provided and the inter-operator/inter-patient/inter-medical facility variability that may result in treatment inefficiencies may be reduced.

Figure 5:
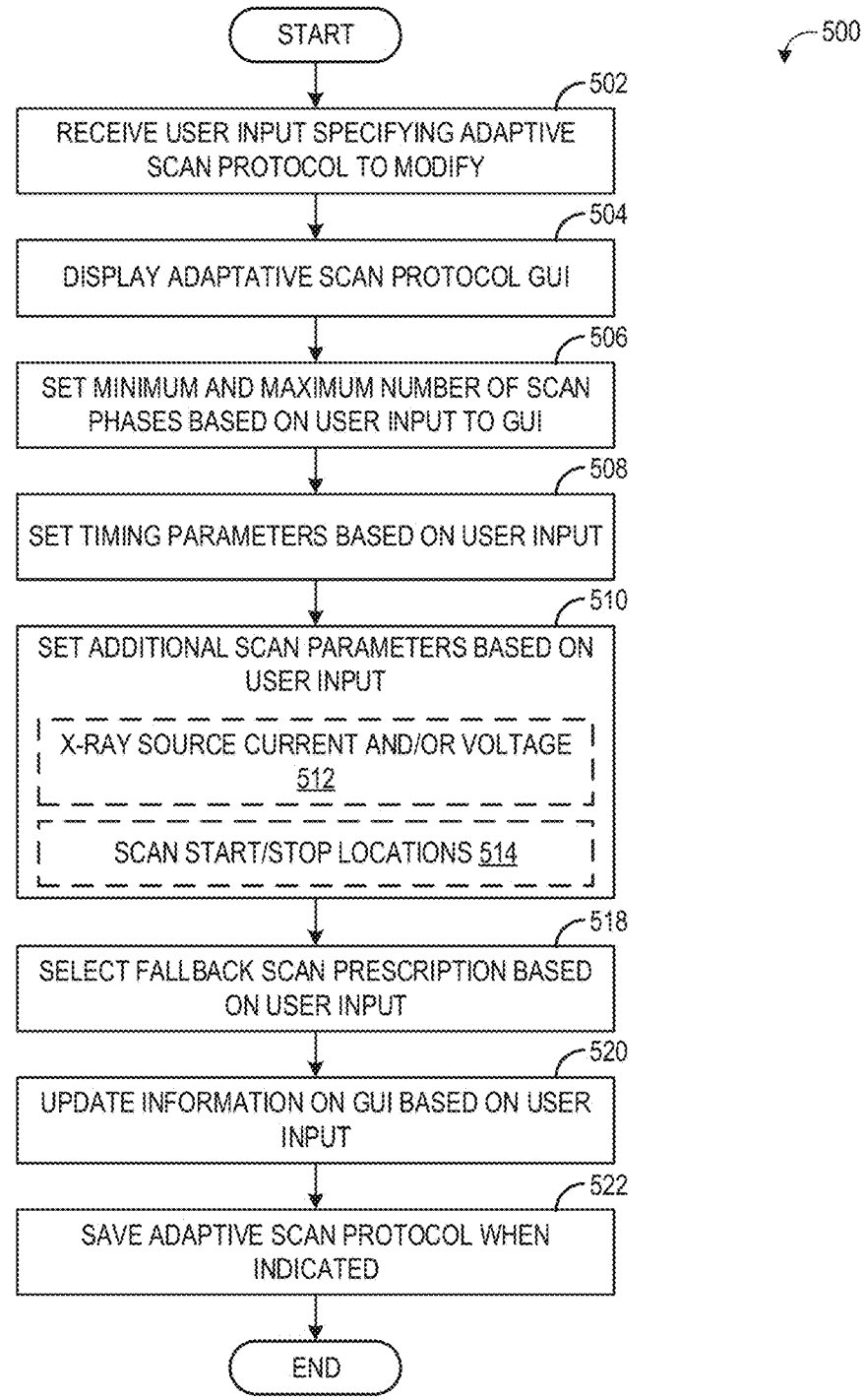
FIG. 5 is a flow chart illustrating a method for setting adaptive contrast scan settings in advance via an adaptive scan protocol graphical user interface (GUI), according to an embodiment.

Therefore, FIG. 5 shows a flow chart illustrating a method 500 for defining an adaptive contrast scan protocol that may be used to tailor a contrast scan prescription to each patient with no prior knowledge of the patient's hemodynamics and age. In particular, method 500 may be executed at a time that is not concurrent with performing the scan protocol in order to set default scan parameters that will be pre-loaded at scan time upon selection of the corresponding protocol. Method 500 is described with respect to the system and components described above with respect to FIGS. 1-2 but may be carried out with other systems/components without departing from the scope of this disclosure. Method 500 may be carried out according to instructions stored in non-transitory memory of a computing device (e.g., computing device 216 of FIG. 2). Method 500 may include the selection/adjustment of various parameters for one or more contrast scan protocols. Thus, method 500 may be performed in response to authenticating an authorized personnel, such as a lead technologist, protocol manager, radiologist, hospital administrator, etc.

At 502, a user input specifying an adaptive scan protocol to modify is received. In some examples, the computing device may store a plurality of default contrast scan protocols, and the user input may include a selection of one of the default contrast scan protocols. In other examples, the computing device may store one or more modified contrast scan protocols, and the user input may include a selection of one of the modified contrast scan protocols. In still further examples, the user input may include an indication that a new contrast scan protocol is to be defined. In the present example, the contrast scan protocol is an mCTA protocol. However, in other examples, the contrast scan protocol may be another suitable contrast scan protocol, such as a CTP, a CTA followed by a CTP, a CTP followed by a CTA, a combined CTP and CTA, a CTA, a virtual mCTA, or another contrast scan. The contrast scan protocol may be specific to a particular anatomy and/or a particular suspected patient condition. For example, the contrast scan protocol may be specific to a head, head/neck, abdomen, heart, etc., and/or the contrast scan protocol may be specific to acute stroke, myocardial infarction, liver dysfunction, etc. Further, additionally or alternatively, the contrast scan protocol may be specific to a type of patient, such as pediatric, adult, advanced age adult, small, medium, large, etc. The user input may be received from a suitable user input device, such as the operator console 220 of FIG. 2 (which may include a keyboard, a mouse, a touchscreen, and/or another suitable input device).

At 504, an adaptive scan protocol graphical user interface (GUI) is displayed. The adaptive scan protocol GUI may be displayed on a display device communicatively coupled to the computing device, such as display device 232 of FIG. 2. The adaptive scan protocol GUI may include one or more sections via which various parameters for the contrast scan protocol may be set/adjusted. Further, in some examples, the adaptive scan protocol GUI may include a visual representation of the acquisitions and timings for the scan protocol that may change as the user enters input to adjust/set the scan parameters.

At 506, a minimum and maximum number of scan phases is set based on user input to the adaptive scan protocol GUI. As explained above, the scan protocol may include different scan parameters that may be adjusted as the contrast scan progresses. As will be elaborated herein, the contrast scan may be adjusted based on a patient marker (e.g., an arterial peak time) that is determined using information received as the scan progresses. Depending on the contrast scan protocol being defined, the contrast scan protocol may include a variable number of scan phases that is adjusted based on the patient marker or a fixed number of scan phases. When a fixed number of scan phases is used, the user may set the fixed number of scan phases to use as a single value (or, the minimum number and the maximum number may be set to the same value). When a variable number of scan phases is used, the user may set both the minimum number of scan phases and the maximum number of scan phases, with the minimum number less than the maximum number. As will be elaborated below with respect to FIGS. 7-10, the minimum number of scan phases and the maximum number of scan phases may each be constrained to a pre-determined allowable range of clinically relevant values. Thus, when the scan protocol is executed at scan time, the scan prescription will include no less than the minimum number of scan phases and no more than the maximum number of scan phases.

At 508, timing parameters are set based on user input to the adaptive scan protocol GUI. Depending on the contrast scan protocol being defined, the contrast scan protocol may include a fixed amount of time (e.g., time duration, also referred to herein as tau) between each scan phase or a variable amount of time between each scan phase, which may be adjusted based on the patient marker. Thus, the timing parameters may include, for example, one or more of a fixed amount of time between each scan phase, a minimum amount of time between each scan phase, a maximum amount of time between each scan phase, an adjustment increment, a minimum total scan time, and a maximum total scan time. When a fixed amount of time between phases is used, the user may set the fixed amount of time between phases to a single value (or, the minimum amount of time and the maximum amount of time are set to the same value). When a variable amount of time between each scan phase is used, the user may set both the amount of time between each scan phase and the maximum amount of time between each scan phase, with the minimum amount of time between each scan phase constrained to be less than the maximum amount of time between each scan phase. As will be elaborated below with respect to FIGS. 7-10, the minimum amount of time between each scan phase and the maximum amount of time between each scan phase may each be further constrained to a pre-determined allowable range of clinically relevant values. Thus, when the scan protocol is executed at scan time, an amount of time between each scan phase will be no less than the minimum amount of time between each scan phase and no more than the maximum amount of time between each scan phase.

Further, setting the timing parameters may include setting a plurality of timing ranges for the patient marker. Each timing range may correspond to a prescribed number of phases and/or amount of time between each phase. For example, for each timing range, the user may indicate a minimum and/or maximum amount of time for the timing range and the corresponding number of phases and/or amount of time between phases to use for when the patient marker is within that timing range. The adjustment increment may refer to a change in the time between phases for each timing range, as will be elaborated below with particular respect to FIG. 8.

At 510, additional scan parameters may be set based on user input to the adaptive scan protocol GUI. The additional scan parameters may include x-ray source current and/or voltage, as indicated at 512. For example, when the imaging system is a CT system as described herein or another x-ray imaging system, the output of the x-ray source may be adjustable by the user. The adaptive scan protocol GUI may include a current input for each phase, and the x-ray source current for each phase may be adjusted by the user via input to the current inputs.

In some examples, the additional scan parameters may include scan start/stop locations, as indicated at 514. In such examples, the adaptive scan protocol GUI may include start/stop location inputs for each acquisition, and the user may adjust the scan start/stop location via the inputs, if desired. For example, the user may set three locations for the scan start and end: the top of the head, the bottom of the neck, and the bottom of the head. Further, in some examples, the location of the top of the head may be determined from a non-contrast head scan performed at the scan time, as will be described below with respect to FIG. 11. Thus, the top of the head location may be set explicitly or set to be determined via the non-contrast head scan. Further, the user may prescribe secondary reconstruction and auto batch reformats for each scan phase. As will be elaborated below with respect to FIG. 6, a GUI (e.g., widget) for setting an adaptive multi-phase reconstruction prescription may enable the user (e.g., the lead technician) to set the secondary reconstruction and auto batch reformats ahead of time.

It is to be understood that the additional scan parameters discussed herein are exemplary, and other scan parameters may be adjusted without departing from the scope of this disclosure.

At 518, a fallback scan prescription may be set based on user input to the adaptive scan protocol GUI. As explained above, the scan protocol may include making adjustments to the scan prescription, such as the number of phases and/or amount of time between each phase, as the scan progresses based on the patient-specific markers that is detected in-flight (e.g., while the scan is progressing) or just prior to the scan (e.g., via a timing bolus). If the patient marker cannot be detected, or if adjustments can otherwise not be communicated to the system, the scan prescription that is executed based on the scan protocol may not function, or may not function as intended, which may impact diagnostic image quality. Thus, to prevent such issues, the fallback scan prescription may be set so that it may be executed if the prescription cannot be updated in-flight for any reason. The adaptive scan protocol GUI may include a fallback scan prescription section where the user may specify timing and parameters of the fallback scan prescription, such as the number of phases and the amount of time between phases for the fallback scan prescription.

At 520, the information that is displayed via the adaptive scan protocol GUI may be updated as the user enters the user input described above. For example, when the user enters input to adjust a timing range for the patient marker, the input for that timing range may be updated to reflect the adjusted timing range. Further, the adaptive scan protocol GUI may include a preview section that displays a visual representation of the scan protocol, where a generic/base contrast agent curve (e.g., an AIF curve) is displayed and the timing of each scan acquisition is displayed as part of the curve. If a parameter is adjusted, the preview section may be adjusted in a corresponding manner. Additional details of the adaptive scan protocol GUI are discussed below with respect to FIGS. 7-10.

At 522, the adaptive scan protocol is saved in memory when indicated (e.g., in response to a user input commanding the protocol be saved). The saving of the scan protocol may include saving any adjustments made to the scan protocol. The scan protocol may then be retrieved at a later time and executed in order to scan a patient according to the parameters specified in the scan protocol, as will be explained below with respect to FIG. 11. Method 500 may then end.

Typically, a technologist will perform multiple steps of manual adjustments to begin image reformats during a scan. Reformatting includes an image reconstructor (e.g., the image reconstructor 230 of FIG. 2) interpolating two-dimensional multi-slice images acquired during an axial scan to generate a three-dimensional volume. The three-dimensional volume may be subsequently used to create two-dimensional images in any plane. For example, a first phase acquisition includes a head and neck acquisition that starts at the bottom of the neck (e.g., at the aortic arch) and stops at the top of the head. The first phase acquisition may be used as a regular (e.g., single phase) CTA in order to assess if there is an occluding clot, where it is located, and how to guide a catheter if a thrombectomy is to be performed. When multi-phase CTA is performed, the first phase acquisition also serves as a first phase of the mCTA, which is used to assess collateral blood flow. However, subsequent phases of the mCTA (e.g., phases 2 through N) include head-only acquisitions that scan from the bottom of the head to the top of the head. For the mCTA to be reconstructed, the first phase needs to be cropped/reconstructed to match the same coverage as the subsequent phases. As a result, the mCTA reconstruction is delayed until the technologist manually crops and reconstructs the head-only portion of the first phase acquisition. Since each phase of the multi-phase scan has its own reformat, adjusting the number of phases for the scan in-flight may result in manually adding associated reformats for the number of phases that are ultimately acquired. This may be time consuming and increase an amount of time before a diagnosis can be made.

Figure 6:
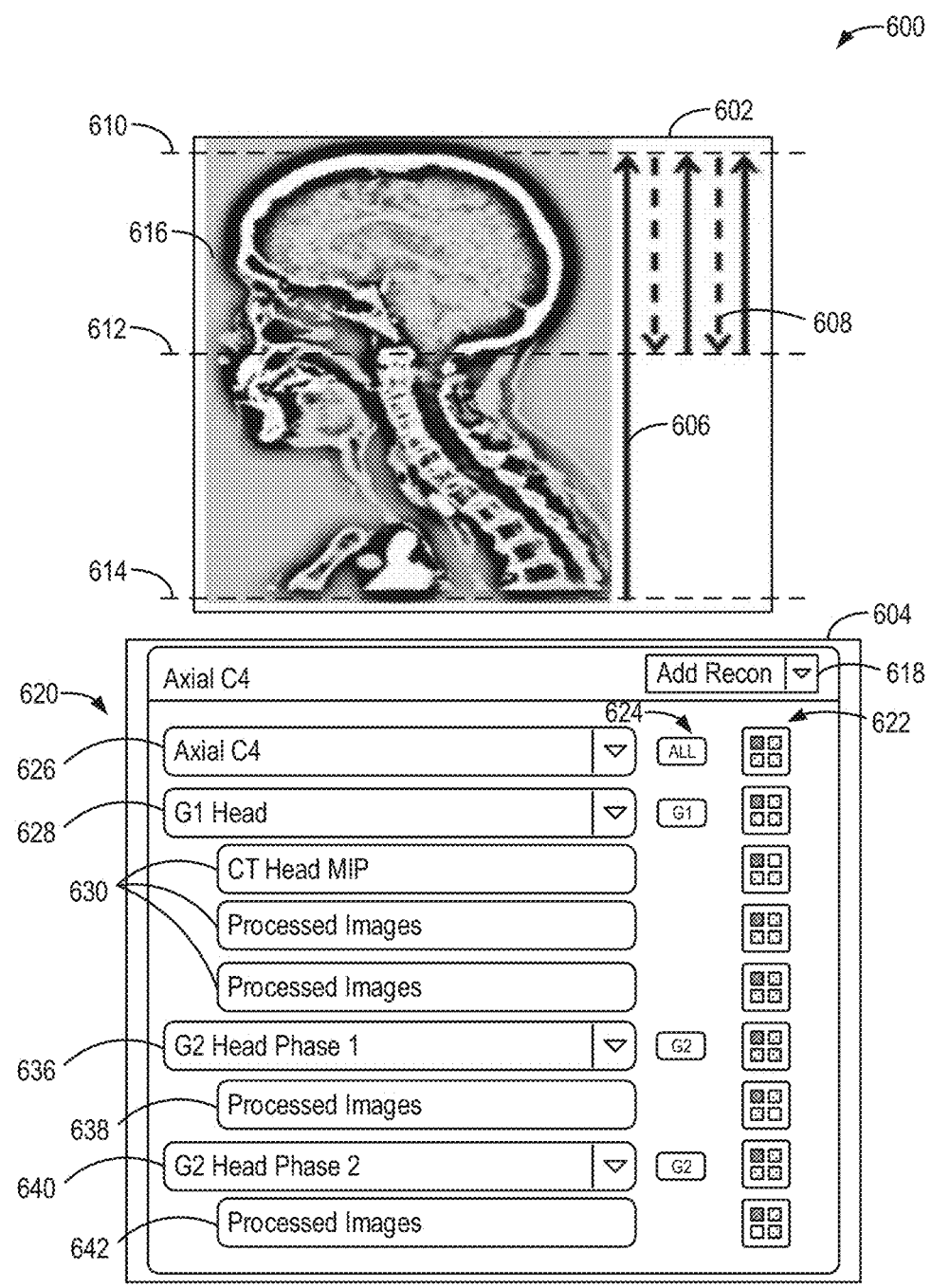
FIG. 6 shows an example GUI for setting an adaptive multi-phase reconstruction prescription, according to an embodiment.

Therefore, FIG. 6 shows an example adaptive multi-phase reconstruction prescription GUI 600. A lead technician, for example, may use the GUI 600 to prescribe a reconstruction series to batch reformat the entire series. The system may then auto batch the reformats at the scan time to reduce or eliminate manual reformats at the scan time.

The GUI 600 includes a preview section 602 and a reconstruction prescription section 604. The preview section 602 includes a generic (e.g., not patient-specific) reconstructed image 616 including a view of a head and neck. The preview section 602 also includes a plurality of solid arrows 606 that indicate table movement in a scanning direction (e.g., during an acquisition) and a plurality of dashed arrows 608 that indicate table movement in a return direction between each phase in the scan. Three scan start/stop locations are shown as a first location marker 610, a second location marker 612, and a third location marker 614, each represented by a dashed line. The first location marker 610 corresponds to the top of the head, the second location marker 612 corresponds to the bottom of the head, and the third location marker 614 corresponds to the bottom of the neck.

The lead technician may set the second location marker 612 and the third location marker 614 relative to the first location marker 610 (e.g., the top of the head). For example, the second location marker 612 may be set to be a first distance (e.g., 14 centimeters) offset from (e.g., below) the first location marker 610. Similarly, the third location marker 614 may be set to be a second distance (e.g., 36 centimeters) from the first location marker 610. As an example, the lead technician may drag and drop the dashed line representing each location marker to adjust the locations relative to the generic reconstructed image 616 and/or relative to each other. Thus, at scan time, a user performing the scan may only explicitly set the first location marker 610, and the second location marker 612 and the third location marker 614 may be automatically positioned relative to the set first location marker 610 based on the first distance and the second distance pre-set by the lead technician. In other examples, the first location marker 610 may be positioned automatically based on data from a non-contrast head series or images collected from a camera system and using visual recognition algorithms, and the user may not explicitly set the first location marker 610.

The reconstruction prescription section 604 defines a prescription that will be used for reconstructing images and includes an add recon user input 618 and a plurality of user selections 620. The add recon user input 618 contains a selectable option to allow the lead technician to directly select between a head and neck reconstruction and a head only reconstruction. As one example, the lead technician may prescribe scan phase G1 (e.g., group 1, or the first phase acquisition) as head and neck or as head only. If G1 is set to head only, it may take its reconstruction start location from G2 (e.g., group 2, or the second phase acquisition). Because G2 is a head-only scan, the start location is the bottom of the head. Thus, when "G1 head" is selected, as shown, "all" refers to the series with all phases (including G1), and only the head range is reconstructed (and not the neck range of the G1 scan). If one or more phases is not performed at scan time, for example, due to the patient having a short arterial peak time, then reconstructions associated with the one or more phases are also not performed. The reconstruction prescription section 604 also includes a summary column 624 that indicates what each user selection prescribes (e.g., all, G1, G2) and a viewpoint column 622 to indicate which viewport a particular reconstruction will be displayed in (e.g., via a shaded box). In the example shown, there are four possible viewports arranged in a grid, although other numbers and arrangements are also possible.

The plurality of user selections 620 includes a scan type user input 626. The scan type user input 626 may be a drop down menu, for example, that enables the lead technician to select from a plurality of different scan types, which may be axial or helical, for example. In the example shown, an axial C4 scan is selected, meaning that the scan type being prescribed is an axial scan that goes from the top of the head through the C4 vertebrae. The plurality of user selections 620 further includes a G1 user input 628, a G2 phase 1 user input 636, and a G2 phase 2 user input 640. In the example shown, the G1 user input 628 is a drop down menu that enables the user to select between head and neck reconstruction and a head only reconstruction for the G1 phase. In the example show, the head only reconstruction is selected. Further, the G1 user input 628 serves as a header for additional G1-specific user inputs 630, shown as soft buttons in the example of FIG. 6. By selecting the appropriate soft button, the user may trigger post-process outputs that use the reconstructions as input to the post-process. In the example shown, the post-process outputs include a maximum intensity projection (MIP) and processed images. The G2 phase 1 user input 636 includes a G2 phase 1 button 638, and the G2 phase 2 user input 640 includes a G2 phase 2 button 642. Additional phase user inputs may be added in response to the user adding a reconstruction via the add recon user input 618, for example.

In this way, the lead technician may specify reconstruction of the head portion of the G1 phase ahead of time. As a result, the reconstruction may be performed automatically, with the reconstruction start location set to the bottom of the head based on the G2 phase start location. By performing the reformats automatically instead of manually, an amount of time before a diagnostic image is achieved is reduced.

Figure 7:
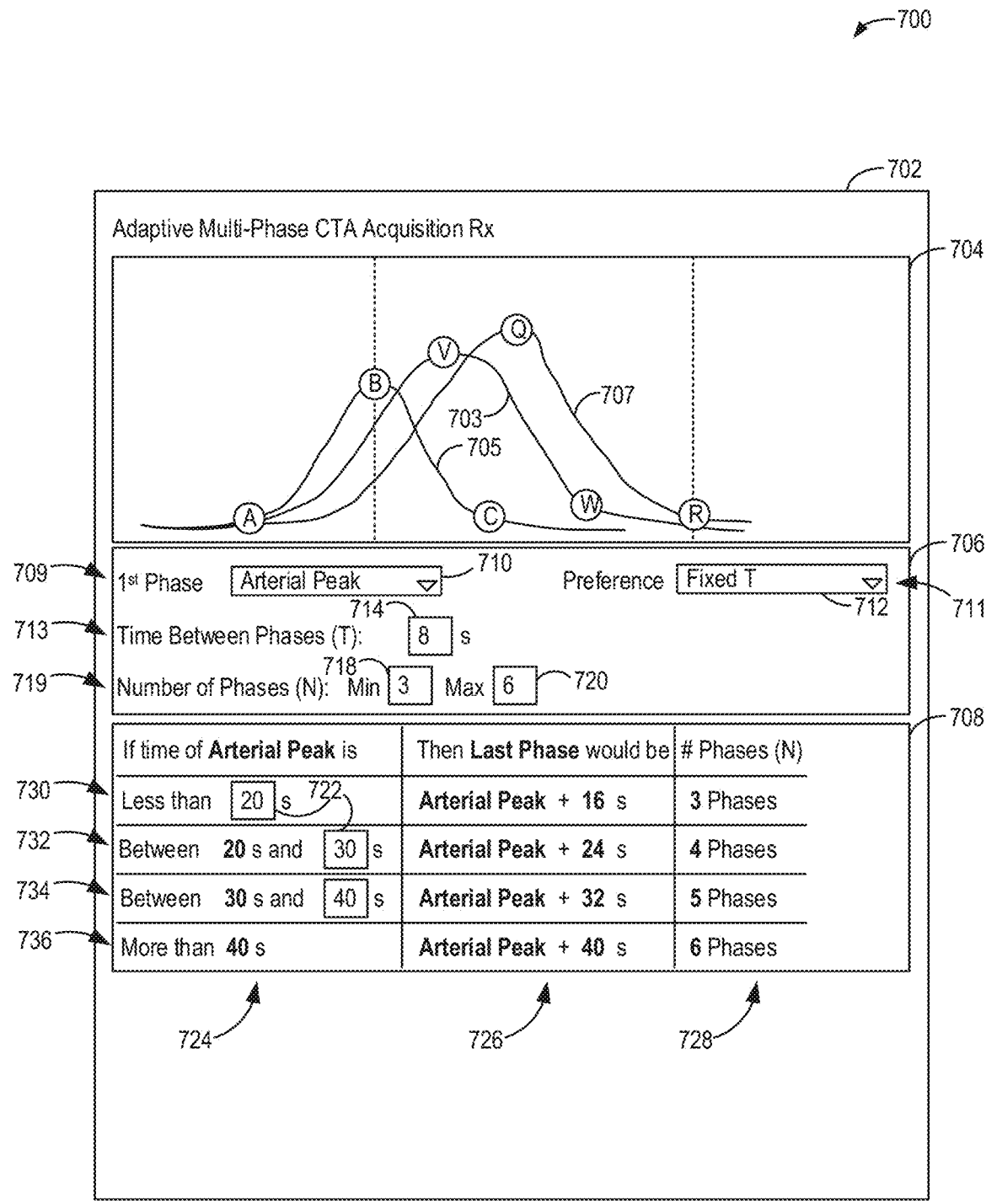
FIG. 7 shows a first example GUI for setting an adaptive multi-phase contrast scan protocol, according to an embodiment of the disclosure.

Turning now to FIG. 7, an example adaptive mCTA scan protocol GUI 700 that may be displayed on a display device (e.g., display device 232 shown in FIG. 2) in response to a user request to modify an existing adaptive mCTA scan protocol or in response to a user request to establish a new adaptive mCTA scan protocol is shown. The adaptive mCTA scan protocol GUI 700 is a non-limiting example of the adaptive scan protocol GUI that is displayed as part of method 500 of FIG. 5. The adaptive mCTA scan protocol GUI 700 shown in FIG. 7 is specific to a multi-phase angiography scan protocol, but it is to be understood that a similar adaptive scan protocol GUI may be displayed in order to set parameters for other types of contrast scans.

The adaptive mCTA scan protocol GUI 700 includes a widget 702. The widget 702 may be divided into a preview section 704, a prescription overview section 706, and a detailed prescription section 708. However, other groupings and arrangements of parameters and scan information are also possible, and the layout shown in FIG. 7 is one example of how the widget 702 may be arranged. The preview section 704 depicts a low-fidelity, generic (e.g., non-patient specific) example visual representation of an adaptive mCTA scan, including a generic AIF curve 705, a generic VOF curve 707, and a generic TUC 703, which may be similar to the AIF curve 402, the VOF curve 404, and the TUC 406 described with respect to FIG. 4, for example. The preview section 704 may further include a plurality of lines depicting an overall scan time range for the mCTA, such as extending from point B (arterial peak) to point R (venous return to baseline).

The prescription overview section 706 includes a plurality of user interface control inputs via which the user may define how many scan phases are to be performed and set values related to the timing of each phase. In the example shown, the prescription overview section 706 includes a first phase input 709, a protocol input 711, a time between phases input 713, and a number of phases input 719. The first phase input 709 may be a drop down menu that includes a plurality of selectable options for defining a marker for the first phase of the mCTA scan, and all other phases may be acquired relative to the selected first phase. The marker for the first phase of the mCTA scan may also represent a hemodynamic marker of a patient to use for adapting a scan prescription when the adaptive mCTA scan protocol is executed. In the example shown, an arterial peak option 710 is selected within the first phase input 709. The protocol input 711 may be a drop down menu that includes a plurality of selectable options for defining protocol preferences. As one example, the user interface control inputs may vary based on the option selected in the protocol input in order to tailor the protocol toward the preference selected, as will be elaborated with respect to FIGS. 8-10. However, in other examples, the protocol input 711 may be omitted from the widget 702, and different widgets may be used to define protocols with different preferences instead of a single widget adapting to accommodate different protocol preferences.

In the example shown, a fixed timing ("fixed T") option 712 is selected within the protocol input 711. Because the fixed timing option 712 is selected, the time between phases input 713 includes a single time parameter 714. The time parameter 714 may be adjusted by the user to define an amount of time (e.g., in seconds) between each phase of the mCTA. Further, the time parameter 714 may be constrained to a pre-programmed allowable range defined by a minimum value (e.g., 5 seconds) and a maximum value (e.g., 11 seconds). The allowable range may include a clinically relevant range of values to ensure that the user cannot enter values (e.g., in error) that are not clinically relevant. As an example, if the pre-programmed minimum value is 5 seconds and the user enters "3," the GUI 700 may automatically correct the input value to "5" (e.g., the closest value within the allowable range). As another example, if the pre-programmed maximum value is 11 seconds and the user enters "20," the GUI may automatically correct the input value to "11". In other examples, the GUI 700 may not accept the input (and may not display a value for the time parameter 714) if the input value is not within the allowable range. In still other examples, additionally or alternatively, the GUI 700 may output a warning and communicate the allowable range to the user (e.g., via a pop-up message). In the example shown, the time parameter is set to 8 seconds, meaning that 8 seconds will elapse between each scan phase no matter how many phases are prescribed.

The number of phases input 719 includes a minimum number parameter 718 and a maximum number parameter 720. Similar to the time parameter 714, the minimum number parameter 718 and the maximum number parameter 720 may each include a pre-programmed allowable range defined by a minimum value and a maximum value for the corresponding parameter. For example, the minimum number parameter 718 may be constrained to an integer between 2 and 8, for example, and the maximum number parameter 720 may be constrained to an integer between 6 and 15. Further, the minimum number parameter 718 and the maximum number parameter 720 may be constrained relative to each other so that the minimum number parameter 718 does not exceed the maximum number parameter 720 (e.g., the minimum number parameter 718 is constrained to be less than or equal to the maximum number parameter 720). In the example shown, the minimum number parameter 718 is set to 3 and the maximum number parameter 720 is set to 6, meaning that the mCTA scan prescription will include no fewer than 3 scan phases and no more than 6 scan phases.

The detailed prescription section 708 includes a table (e.g., a lookup table) that describes a plurality of possible scan prescriptions given the parameters selected in the prescription overview section 706 and includes a plurality of additional timing parameter inputs 722. The additional timing parameter inputs 722 enable the user to specify timing breakpoints at which the system should dynamically increase/decrease the number of phases for the mCTA (e.g., defines the timing ranges described above with respect to FIG. 5). A header section describes the values given in each column. Because the adaptive mCTA scan protocol is adjusted based on the marker (e.g., the arterial peak time), as described above with respect to FIG. 5, a column 724 of the table describes the time to the arterial peak relative to different time ranges given by each row. A column 726 of the table describes the timing of a last phase of the scan relative to the arterial peak. A column 728 of the table describes the number of phases that will be performed based on the arterial peak time relative to the time ranges given in each row. Further, in the example shown, the bolded text represents dynamic labeling that is directly or indirectly defined by the explicit parameters input into the prescription overview section 706 and the additional timing parameter inputs 722.

A number of rows in the table is a function of the parameters defined in the prescription overview section 706. For example, the number of rows may increase as the maximum number parameter 720 further increases above the minimum number parameter 718 given in the number of phases input 719. In the example shown, the detailed prescription section 708 includes a first row 730 defining the mCTA scan prescription when the marker (e.g., the arterial peak) is less than a first timing parameter input, a second row 732 defining the mCTA scan prescription when the marker is between the first timing parameter input (which is input in the first row 730) and a second timing parameter input, a third row 734 defining the mCTA scan prescription when the marker is between the second timing parameter input (which is input in the second row 732) and a third timing parameter input, and a fourth row 736 defining the mCTA scan prescription when the marker is greater than the third timing parameter input (which is input in the third row 734). Each of the plurality of additional timing parameter inputs 722 may be constrained such that each parameter value is greater than that given in the previous row.

The information given detailed prescription section 708 will now be described based on the example parameters shown in the prescription overview section 706 and the detailed prescription section 708, although other parameters are also possible. In the example shown in FIG. 7, the first timing parameter input is 20 seconds. Thus, the first row 730 indicates that the adaptive mCTA scan prescription will include 3 phases, with the last phase occurring 16 seconds after the arterial peak (e.g., the first phase plus two additional phases each spaced 8 seconds apart), when the time of the arterial peak is less than 20 seconds. The second timing parameter input is 30 seconds. Thus, the second row 732 indicates that the adaptive mCTA scan prescription will include 4 phases, with the last phase occurring 24 seconds after the arterial peak (e.g., the first phase plus three additional phases each spaced 8 seconds apart), when the time of the arterial peak is between 20 and 30 seconds. The third timing parameter input is 40 seconds. Thus, the third row 734 indicates that the adaptive mCTA scan prescription will include 5 phases, with the last phase occurring 32 seconds after the arterial peak (e.g., the first phase plus four additional phases each spaced 8 seconds apart), when the time of the arterial peak is between 30 and 40 seconds. The fourth row 736 indicates that the adaptive mCTA scan prescription will include 6 phases, with the last phase occurring 40 seconds after the arterial peak (e.g., the first phase plus give additional phases each spaced 8 seconds apart), when the time of the arterial peak is more than 40 seconds. As such, the user (a lead technologist) may use the widget 702 of the GUI 700 to fully prescribe a fixed timing adaptive mCTA protocol.

Figure 8:
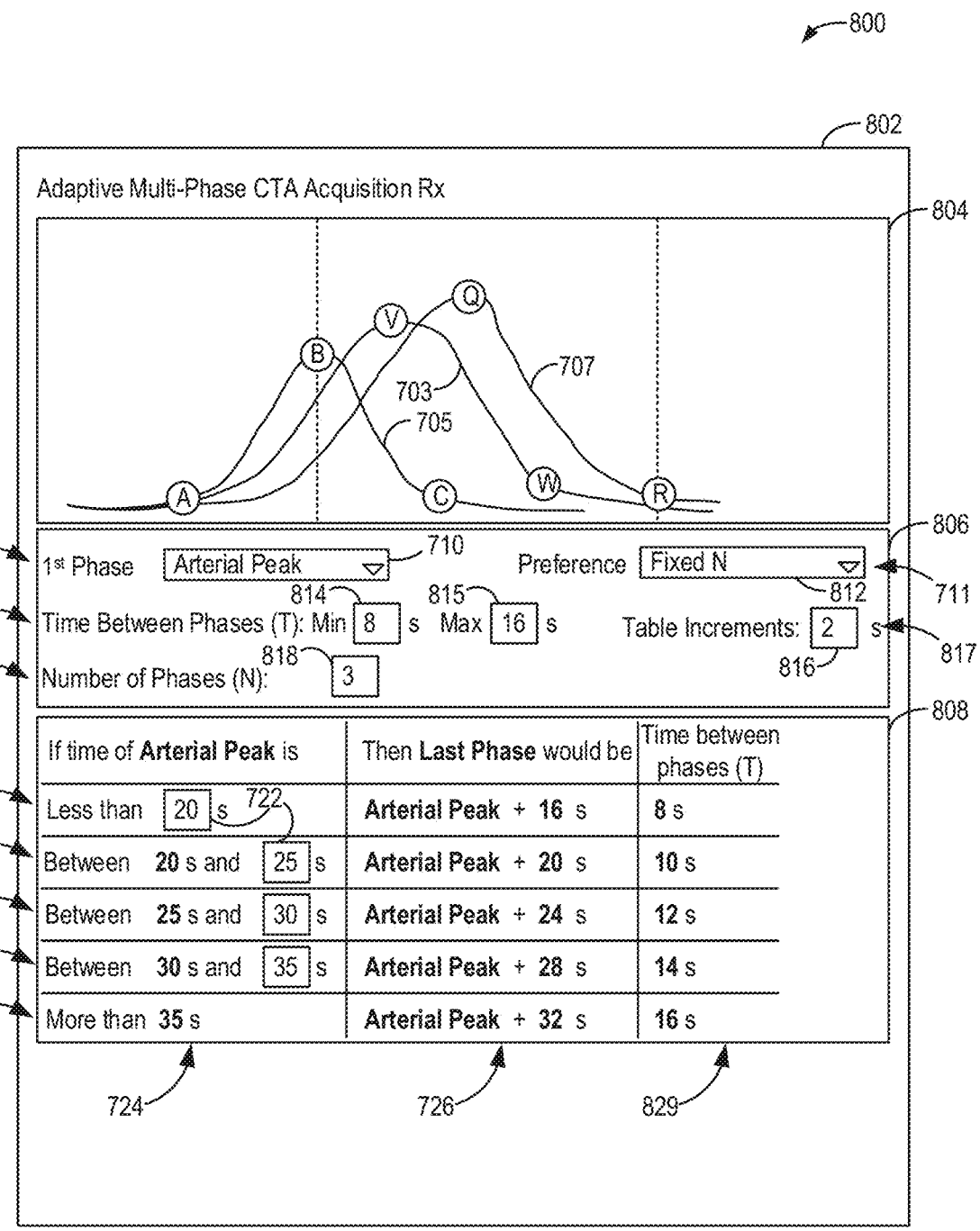
FIG. 8 shows a second example GUI for setting an adaptive multi-phase contrast scan protocol, according to another embodiment of the disclosure.

FIG. 8 shows an example adaptive mCTA scan protocol GUI 800. The GUI 800 may be the GUI 700 of FIG. 7 in an adjusted state. Alternatively, the GUI 800 may be a separate interface that is independent from the GUI 700 while containing similar information. Aspects of FIG. 8 that are the same as those described with respect to the GUI 700 of FIG. 7 are numbered the same and function as previously described.

Similar to the GUI 700, the GUI 800 includes a widget 802 divided into a preview section 804, a prescription overview section 806, and a detailed prescription section 808. In the example shown, the preview section 804 includes the generic AIF curve 705, the generic VOF curve 707, and the generic TUC 703, as described above with respect to FIG. 7. The prescription overview section 806 is similar to the prescription overview section 706 of FIG. 7, with the arterial peak option 710 selected for the first phase input 709. However, in GUI 800, a fixed number of phases ("fixed N") option 812 is selected within the protocol input 711. Because the fixed number of phases option 812 is selected, a time between phases input 813 includes a minimum time parameter 814 and a maximum time parameter 815, in contrast to the single time parameter 714 of the time between phases input 713 (see FIG. 7). The minimum time parameter 814 and the maximum time parameter 815 each may be constrained to a pre-programmed clinically relevant range, such as described above. As one example, the minimum time parameter 814 may be constrained to be in range from 2 to 8 seconds. As another example, the maximum time parameter 815 may be constrained to be in a range from 6 to 15 seconds. In the example shown, the minimum time parameter 814 is set to 8 seconds and the maximum time parameter 815 is set to 16 seconds, meaning that no less than 8 and no more than 16 seconds will elapse between each phase of the mCTA scan.

The prescription overview section 806 also includes a table increment input 817 for entering a table increment parameter 816. The table increment parameter 816 defines a time increment between each change in the time between phases, as will be elaborated below with respect to the detailed prescription section 808. The table increment parameter 816 may be constrained to be within a pre-programmed, clinically relevant allowable range that is less than the minimum time parameter 814. For example, the allowable range may span between 1 to 3 seconds, meaning that the table increment parameter 816 can be no less than 1 second and no more than 3 seconds.

Further, because the fixed number of phases ("fixed N") option 812 is selected within the protocol input 711, a number of phases input 819 includes a single number parameter 818, in contrast to the minimum number parameter 718 and the maximum number parameter 720 for the number of phases input 719 of FIG. 7. The number parameter 818 may be constrained to a pre-programmed clinically relevant range, such as described above. As an example, the number parameter may be constrained to be in a range from 2 to 6 phases. In the example shown, the number parameter 818 is set to 3, meaning that each mCTA scan will include three scan phases, with an amount of time between each phase varying from patient to patient based on a measured or estimated arterial peak time.

The detailed prescription section 808 is similar to the detailed prescription section 708 of FIG. 7, including the column 724 describing the time to the arterial peak relative to different time ranges given by each row, the column 726 describing the timing of a last phase of the scan relative to the arterial peak, and the plurality of additional timing parameter inputs 722. However, the table of the detailed prescription section includes a column 829 that describes a time between phases (T) that will be used based on the arterial peak time relative to the time ranges in each row. Similar to the detailed prescription section 708, the bolded text is dynamic labeling that is directly or indirectly defined by the explicit parameters input into the prescription overview section 806 and the additional timing parameter inputs 722, and the number of rows in the table is a function of the parameters defined in the prescription overview section 806. For example, the number of rows may increase as the maximum time parameter 815 further increases above the minimum time parameter 814 given in the time between phases input 813 and/or the table increment parameter 816 decreases.

In the example shown, the detailed prescription section 808 includes a first row 830 defining the mCTA scan prescription when the marker (e.g., the arterial peak) is less than a first timing parameter input, a second row 832 defining the mCTA scan prescription when the marker is between the first timing parameter input (which is input in the first row 830) and a second timing parameter input, a third row 834 defining the mCTA scan prescription when the marker is between the second timing parameter input (which is input in the second row 832) and a third timing parameter input, a fourth row 836 defining the mCTA scan prescription when the marker is between the third timing parameter input (which is input in the third row 834) and a fourth timing parameter input, and a fifth row 838 defining the mCTA scan prescription when the marker is greater than the fourth timing parameter input (which is input in the fourth row 836). Each of the plurality of additional timing parameter inputs 722 may be constrained such that each parameter value is greater than that given in the previous row. Further, the time between phases increases between consecutive rows down the table by the table increment parameter 816.

The information given detailed prescription section 808 will now be described based on the example parameters shown in the prescription overview section 806 and the detailed prescription section 808, although other parameters are also possible. In the example shown in FIG. 8, the first timing parameter input is 20 seconds. Thus, the first row 830 indicates that the adaptive mCTA scan prescription will include 8 seconds between each of the three phases, with the last phase occurring 16 seconds after the arterial peak, when the time of the arterial peak is less than 20 seconds. The second timing parameter input is 25 seconds. Thus, the second row 832 indicates that the adaptive mCTA scan prescription will include 10 seconds (e.g., 2 seconds more than the previous row having 8 seconds) between each of the three phases, with the last phase occurring 20 seconds after the arterial peak, when the time of the arterial peak is between 20 and 25 seconds. The third timing parameter input is 30 seconds. Thus, the third row 834 indicates that the adaptive mCTA scan prescription will include 12 seconds between each of the three phases, with the last phase occurring 24 seconds after the arterial peak, when the time of the arterial peak is between 25 and 30 seconds. The fourth timing parameter input is 35 seconds. Thus, the fourth row 836 indicates that the adaptive mCTA scan prescription will include 14 seconds between each of the three phases, with the last phase occurring 28 seconds after the arterial peak, when the time of the arterial peak is between 30 and 35 seconds. The fifth row 838 indicates that the adaptive mCTA scan prescription will include 16 seconds between each of the three phases, with the last phase occurring 32 seconds after the arterial peak, when the time of the arterial peak is greater than 35 seconds. As such, the user (a lead technologist) may use the widget 802 of the GUI 800 to fully prescribe a fixed phase number adaptive mCTA protocol.

Figure 9:
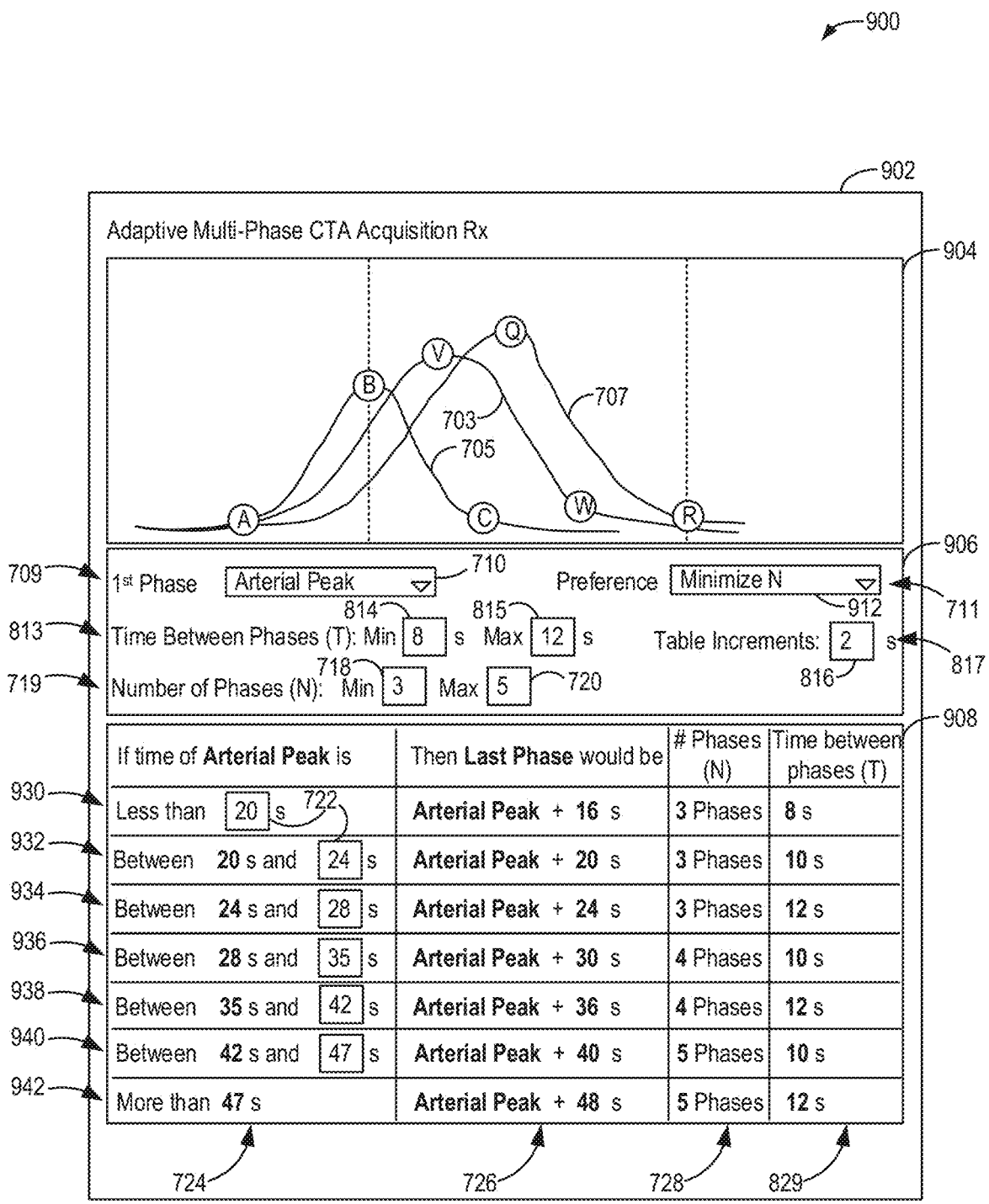
FIG. 9 shows a third example GUI for setting an adaptive multi-phase contrast scan protocol, according to another embodiment of the disclosure.

FIG. 9 shows an example adaptive mCTA scan protocol GUI 900. The GUI 900 may be the GUI 700 of FIG. 7 and/or the GUI 800 of FIG. 8 in an adjusted state. Alternatively, the GUI 900 may be a separate interface that is independent from the GUI 700 and the GUI 800 while containing similar information. Aspects of FIG. 9 that are the same as those described with respect to the GUI 700 of FIG. 7 and the GUI 800 of FIG. 8 are numbered the same and function as previously described.

Similar to the GUI 700 and the GUI 800, the GUI 900 includes a widget 902 divided into a preview section 904, a prescription overview section 906, and a detailed prescription section 908. In the example shown, the preview section 904 includes the generic AIF curve 705, the generic VOF curve 707, and the generic TUC 703, as described above with respect to FIG. 7. The prescription overview section 906 is similar to the prescription overview section 706 of FIG. 7, with the arterial peak option 710 selected for the first phase input 709. However, in GUI 900, a minimize the number of phases ("minimize N") option 912 is selected within the protocol input 711. Because the minimize the number of phases option 912 is selected, the prescription overview section 906 includes the time between phases input 813 and the table increment input 817 described with respect to FIG. 8 and the number of phases input 719 described with respect to FIG. 7. Thus, both the time between phases and the number of phases can be varied in the scan prescription in order to minimize the number of phases performed during the scan.

The detailed prescription section 908 is similar to both the detailed prescription section 708 of FIG. 7 and the detailed prescription section 808 of FIG. 8, including the column 724 describing the time to the arterial peak relative to different time ranges given by each row, the column 726 describing the timing of a last phase of the scan relative to the arterial peak, the column 728 describing the number of phases that will be used based on the arterial peak time, and the column 829 describing a time between phases (T) that will be used based on the arterial peak time relative to the time ranges in each row. Similar to the detailed prescription section 708 and the detailed prescription section 808, the bolded text is dynamic labeling that is directly or indirectly defined by the explicit parameters input into the prescription overview section 906 and the additional timing parameter inputs 722, and the number of rows in the table is a function of the parameters defined in the prescription overview section 906. For example, the number of rows may increase as the maximum time parameter 815 further increases above the minimum time parameter 814, the maximum number parameter 720 further increases above the minimum number parameter 718, and/or the table increment parameter 816 decreases.

In the example shown, the detailed prescription section 908 includes a first row 930 defining the mCTA scan prescription when the marker (e.g., the arterial peak) is less than a first timing parameter input, a second row 932 defining the mCTA scan prescription when the marker is between the first timing parameter input (which is input in the first row 930) and a second timing parameter input, a third row 934 defining the mCTA scan prescription when the marker is between the second timing parameter input (which is input in the second row 932) and a third timing parameter input, a fourth row 936 defining the mCTA scan prescription when the marker is between the third timing parameter input (which is input in the third row 934) and a fourth timing parameter input, a fifth row 938 defining the mCTA scan prescription when the marker is between the fourth timing parameter input (which is input in the fourth row 936) and a fifth timing parameter input, a sixth row 940 defining the mCTA scan prescription when the marker is between the fifth timing parameter input (which is input in the fifth row 938) and a sixth timing parameter input, and a seventh row 942 defining the mCTA scan prescription when the marker is greater than the sixth timing parameter input (which is input in the sixth row 940). Each of the plurality of additional timing parameter inputs 722 may be constrained such that each parameter value is greater than that given in the previous row. Further, the time between phases changes by the table increment parameter 816 between consecutive rows in the table.

The information given detailed prescription section 908 will now be described based on the example parameters shown in the prescription overview section 906 and the detailed prescription section 908, although other parameters are also possible. In the example shown in FIG. 9, the first timing parameter input is 20 seconds. Thus, the first row 930 indicates that the adaptive mCTA scan prescription will include three phases with 8 seconds between each phase, with the last phase occurring 16 seconds after the arterial peak, when the time of the arterial peak is less than 20 seconds. The second timing parameter input is 24 seconds. Thus, the second row 932 indicates that the adaptive mCTA scan prescription will include three phases with 10 seconds between each phase, with the last phase occurring 20 seconds after the arterial peak, when the time of the arterial peak is between 20 and 24 seconds. The third timing parameter input is 28 seconds. Thus, the third row 934 indicates that the adaptive mCTA scan prescription will include three phases with 12 seconds between each phase, with the last phase occurring 24 seconds after the arterial peak, when the time of the arterial peak is between 24 and 28 seconds. The fourth timing parameter input is 35 seconds. Thus, the fourth row 936 indicates that the adaptive mCTA scan prescription will include four phases with 10 seconds between each phase, with the last phase occurring 30 seconds after the arterial peak, when the time of the arterial peak is between 28 and 35 seconds. The fifth timing parameter input is 42 seconds. Thus, the fifth row 938 indicates that the adaptive mCTA scan prescription will include four phases with 12 seconds between each phase, with the last phase occurring 36 seconds after the arterial peak, when the time of the arterial peak is between 35 and 42 seconds. The sixth timing parameter input is 47 seconds. Thus, the sixth row 940 indicates that the adaptive mCTA scan prescription will include five phases with 10 seconds between each phase, with the last phase occurring 40 seconds after the arterial peak, when the time of the arterial peak is between 42 and 47 seconds. The seventh row 942 indicates that the adaptive mCTA scan prescription will include five phases with 12 seconds between each phase, with the last phase occurring 48 seconds after the arterial peak, when the time of the arterial peak is greater than 47 seconds. As such, the user (a lead technologist) may use the widget 902 of the GUI 900 to fully prescribe an adaptive mCTA protocol that varies both the number of phases and the time between phases based on the arterial peak time (or other marker) while also minimizing the number of phases in the scan.

Figure 10:
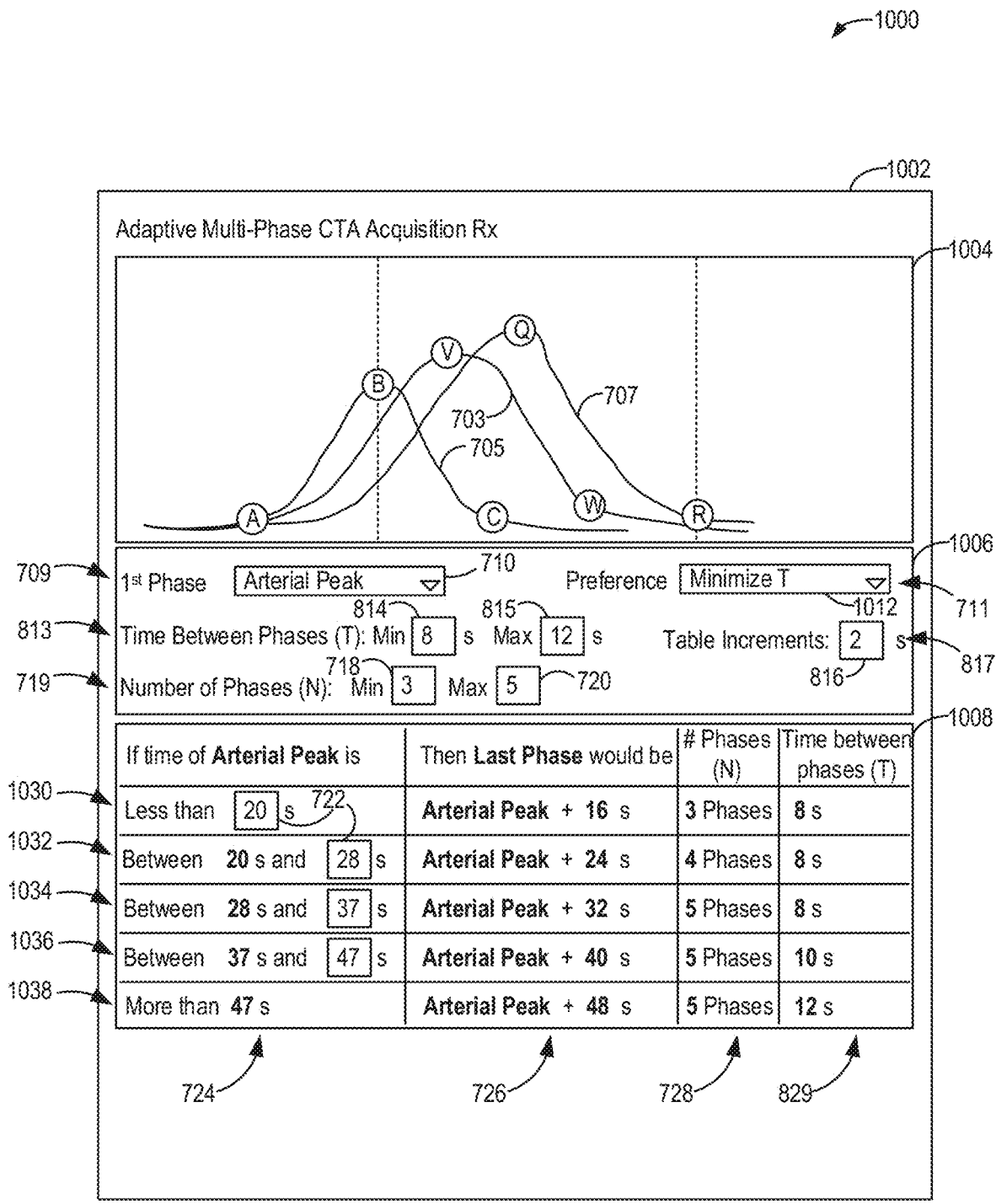
FIG. 10 shows a fourth example GUI for setting an adaptive multi-phase contrast scan protocol, according to another embodiment of the disclosure.
Figure 11:
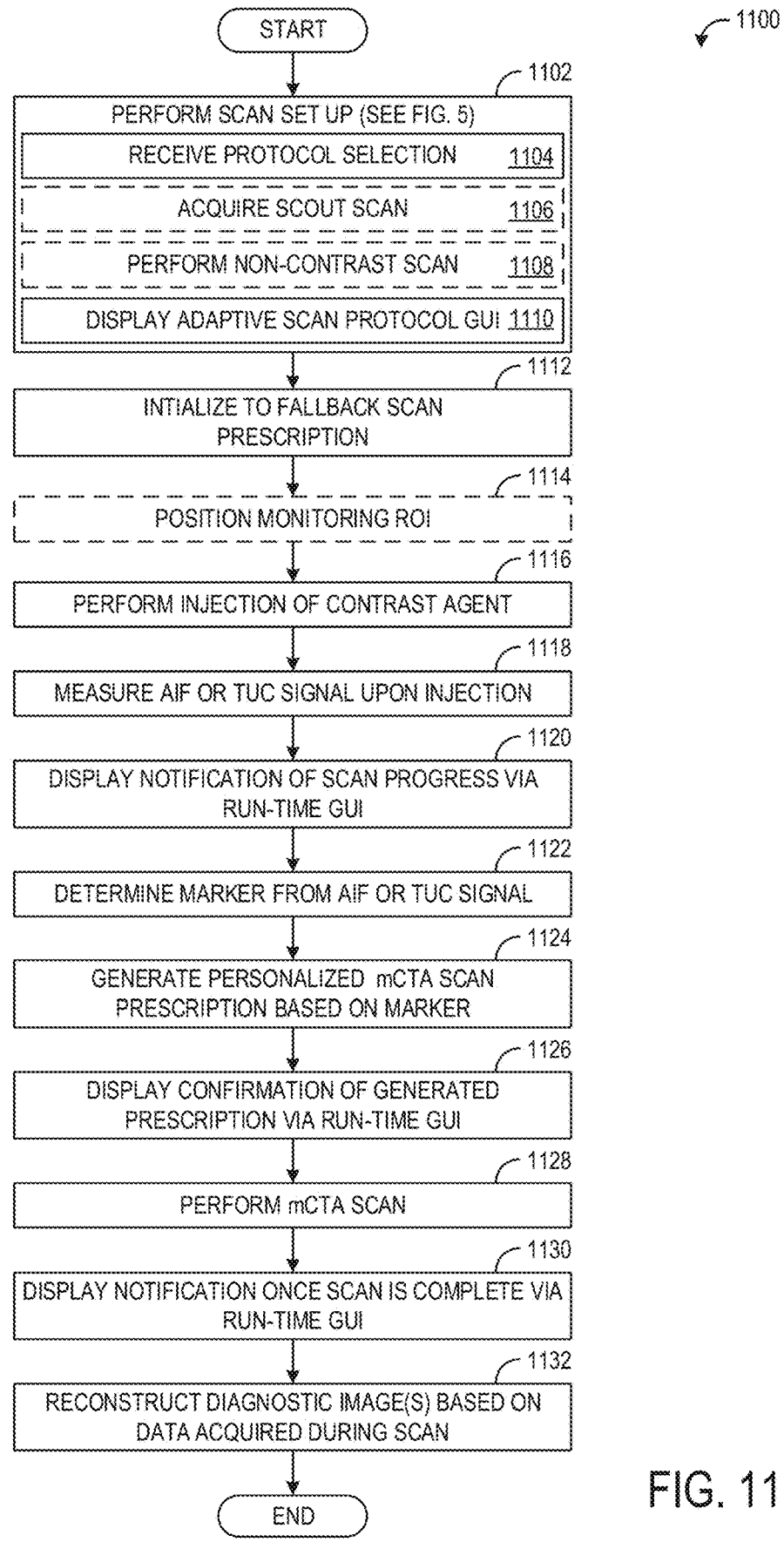
FIG. 11 is a flow chart illustrating a method for performing a personalized multi-phase contrast scan, according to an embodiment of the disclosure.

FIG. 10 shows an example adaptive mCTA scan protocol GUI 1000. The GUI 1000 may be the GUI 700 of FIG. 7, the GUI 800 of FIG. 8, and/or the GUI 900 of FIG. 9 in an adjusted state. Alternatively, the GUI 1000 may be a separate interface that is independent from each of the GUI 700, the GUI 800, and the GUI 900 while containing similar information. Aspects of FIG. 10 that are the same as those described with respect to FIGS. 7-9 are numbered the same and function as previously described.

Similar to the GUIs described with respect to FIGS. 7-9, the GUI 1000 includes a widget 1002 divided into a preview section 1004, a prescription overview section 1006, and a detailed prescription section 1008. In the example shown, the preview section 1004 includes the generic AIF curve 705, the generic VOF curve 707, and the generic TUC 703, as described above with respect to FIG. 7. The prescription overview section 1006 is similar to the prescription overview section 906 of FIG. 9. However, in GUI 1000, a minimize scan time ("minimize T") option 1012 is selected within the protocol input 711. Because the minimize scan time option 1012 is selected, the prescription overview section 1006 includes the time between phases input 813 and the table increment input 817 described with respect to FIG. 8 and the number of phases input 719 described with respect to FIG. 7. Thus, both the time between phases and the number of phases may be varied in the scan prescription in order to minimize the total scan time.

The detailed prescription section 1008 is similar to the detailed prescription section 908 of FIG. 9, including the column 724 describing the time to the arterial peak relative to different time ranges given by each row, the column 726 describing the timing of a last phase of the scan relative to the arterial peak, the column 728 describing the number of phases that will be used based on the arterial peak time, and the column 829 describing a time between phases (T) that will be used based on the arterial peak time relative to the time ranges in each row. As described above, the bolded text is dynamic labeling that is directly or indirectly defined by the explicit parameters input into the prescription overview section 1006 and the additional timing parameter inputs 722. Further, the number of rows may change based on the selections and parameters given in the prescription overview section 1006, as also elaborated above with respect to FIGS. 7-9.

In the example shown, the detailed prescription section 1008 includes a first row 1030 defining the mCTA scan prescription when the marker (e.g., the arterial peak) is less than a first timing parameter input, a second row 1032 defining the mCTA scan prescription when the marker is between the first timing parameter input (which is input in the first row 1030) and a second timing parameter input, a third row 1034 defining the mCTA scan prescription when the marker is between the second timing parameter input (which is input in the second row 1032) and a third timing parameter input, a fourth row 1036 defining the mCTA scan prescription when the marker is between the third timing parameter input (which is input in the third row 1034) and a fourth timing parameter input, and a fifth row 1038 defining the mCTA scan prescription when the marker is greater than the fourth timing parameter input (which is input in the fourth row 1036). Each of the plurality of additional timing parameter inputs 722 may be constrained such that each parameter value is greater than that given in the previous row. Further, the time between phases is constrained to change by the table increment parameter 816 between consecutive rows in the table, although because the minimize scan time option 1012 is selected in the protocol input 711, the time between phases may not change between every consecutive row.

The information given detailed prescription section 1008 will now be described based on the example parameters shown in the prescription overview section 1006 and the detailed prescription section 1008, although other parameters are also possible. In the example shown in FIG. 10, the first timing parameter input is 20 seconds. Thus, the first row 1030 indicates that the adaptive mCTA scan prescription will include three phases with 8 seconds between each phase, with the last phase occurring 16 seconds after the arterial peak, when the time of the arterial peak is less than 20 seconds. The second timing parameter input is 28 seconds. Thus, the second row 1032 indicates that the adaptive mCTA scan prescription will include four phases with 8 seconds between each phase, with the last phase occurring 24 seconds after the arterial peak, when the time of the arterial peak is between 20 and 28 seconds. The third timing parameter input is 37 seconds. Thus, the third row 1034 indicates that the adaptive mCTA scan prescription will include five phases with 8 seconds between each phase, with the last phase occurring 32 seconds after the arterial peak, when the time of the arterial peak is between 28 and 37 seconds. The fourth timing parameter input is 47 seconds. Thus, the fourth row 1036 indicates that the adaptive mCTA scan prescription will include five phases with 10 seconds between each phase, with the last phase occurring 40 seconds after the arterial peak, when the time of the arterial peak is between 37 and 47 seconds. The fifth row 1038 indicates that the adaptive mCTA scan prescription will include five phases with 12 seconds between each phase, with the last phase occurring 48 seconds after the arterial peak, when the time of the arterial peak is greater than 47 seconds. As such, the user may use the widget 1002 of the GUI 1000 to fully prescribe an adaptive mCTA protocol that varies both the number of phases and the time between phases based on the arterial peak time (or other marker) while also minimizing the total scan time.

Next, FIG. 11 shows a flow chart illustrating an example method 1100 for carrying out a personalized mCTA scan. Method 1100 may include setting mCTA scan parameters prior to and during acquisition of the mCTA scan at a time of the scan (in contrast to method 500 of FIG. 5, which includes managing high-level mCTA scan protocols) without prior knowledge of patient physiology. In particular, the present disclosure advantageously recognizes and utilizes a relationship between the arterial peak time, tAp, and a time and duration between tAp and the venous curve return to baseline in order to update the mCTA scan parameters in-flight. Although method 1100 is described with respect to the system and components of FIGS. 1-2, method 1100 could be carried out with other systems/components without departing from the scope of this disclosure. Method 1100 may be carried out according to instructions stored in non-transitory memory of a computing device (e.g., the computing device 216 of FIG. 2). Further, method 1100 may be performed in response to user selection of a scanning protocol that includes an mCTA, such as a stand-alone mCTA, an mCTA followed by a CTP, or a virtual mCTA-from-CTP. In particular, the user may select an adaptive mCTA scan using a user interface, such as will be elaborated below with respect to FIG. 20.

At 1102, method 1100 includes performing scan set up. The scan set up may include both setting up scan parameters and positioning a patient to be scanned. For example, the patient may be placed on a motorized table at a desired position and orientation (e.g., supine and head first). The scan parameters may include, for example, pre-filled and/or adjustable parameters associated with a selected protocol as well as locations for the scan start and end. In some examples, at least a portion of the scan parameters may be determined by a lead technician (or protocol manager) at a previous time (e.g., not concurrent with performing the mCTA scan), as elaborated above with respect to FIG. 5-10. As described above, the lead technician may choose locations for the bottom of the head and the bottom of the neck in terms of a fixed length relative to (e.g., inferior to) the top of the head. Further, the lead technician may prescribe default parameter values for each scan protocol, and the default parameter values may be stored in memory and loaded upon selection of the corresponding protocol.

As such, performing the scan set up may include receiving a protocol selection, as indicated at 1104. For example, a user (e.g., technologist) may select a desired adaptive mCTA scan protocol from a plurality of available protocols. As elaborated above with respect to FIGS. 7-10, the plurality of available protocols may include a first protocol where a timing between mCTA phases is fixed, a second protocol where a number of mCTA phases is fixed, a third protocol where the number of mCTA phases is minimized, and a fourth protocol where scan time is minimized. The user may select the protocol via a drop down menu, such as via the protocol input 711 described with respect to FIGS. 7-11. Further, the selected adaptive mCTA scan protocol may designate a marker to use for updating the mCTA scan prescription in-flight, as will be elaborated below with respect to 1122. The computing device may load the default parameter values set by the lead technologist upon receiving the protocol selection, as mentioned above. Further, the operator performing the scan may select the desired adaptive mCTA scan protocol using a run-time graphical user interface (GUI). The run-time GUI may be displayed on a suitable display device associated with the imaging system, such as display device 232 of FIG. 2. Further, the run-time GUI may present scan information to the operator of the imaging system, such as patient information, scan parameter settings, dose information, etc., as will be explained in more detail below with respect to FIG. 20. However, in other examples, the operator may manually enter the parameter values instead of directly selecting the protocol.

Performing the scan set up optionally includes acquiring a scout scan, as indicated at 1106. The scout scan may include a low-resolution scan that generates 2-dimensional images of the imaging subject from which the scan range/field of view of the following diagnostic scan may be set. The scout scan image may then be used to align the patient and the region of interest within the imaging device. Additionally or alternatively, performing the scan set up optionally includes performing a non-contrast scan, as indicated at 1108. The non-contrast scan may be taken to establish a baseline image for the area to be monitored before delivery of a contrast agent to monitor for brain hemorrhages. For example, a physician may review the non-contrast scan, and the mCTA may proceed if a brain hemorrhage is not present.

Performing the scan set up further includes displaying an adaptive scan protocol GUI, as indicated at 1110. The adaptive scan protocol GUI may be the GUI 700 of FIG. 7, the GUI 800 of FIG. 8, the GUI 900 of FIG. 9, or the GUI 1000 of FIG. 10, for example. Some or all of the adaptive scan protocol GUI may be displayed within or along with the run-time GUI. Via the adaptive scan protocol GUI, the operator may view the set scan parameters for the selected adaptive mCTA scan protocol. In some examples, the operator may adjust the pre-determined scan parameters (e.g., programmed by the lead technologist via the method of FIG. 5) for the current scan via the adaptive scan protocol GUI, similar to the manner described above with respect to FIGS. 5 and 7-10. However, if the operator adjusts any of the scan parameters, the adjustments may not be saved. In this way, one-time adjustments to the adaptive mCTA scan protocol may be made by the operator of the imaging system during a current scan, but the selected adaptive mCTA scan protocol may not be adjusted for subsequent scans. Further, the adaptive mCTA protocol may be confirmed by the user to start the scan via the GUI.

At 1112, method 1100 includes initializing the CT system to perform a fallback scan prescription. The fallback scan prescription may include a maximum number of mCTA phases (e.g., passes) that can be performed during the scan, such as due to time and radiation dosage constraints. Thus, the maximum number of mCTA phases may be a pre-determined number stored in non-transitory memory. As will be elaborated below with respect to FIG. 15, the computing device may initialize the CT system for the maximum number of phases and then trim extra phases that are not indicated according to the adaptive mCTA scan protocol, which may be individualized for the patient and updated mid-scan. Further, the fallback scan prescription may include a pre-determined minimum amount of time between each phase, which may then be adjusted (e.g., increased) in-flight. By initializing the CT system to perform the fallback scan prescription, the computing device may ensure that the CT system is initialized to perform all of the phases that will be prescribed using the adaptive mCTA scan protocol. As such, the system may complete the fallback scan prescription when in-flight prescription updates do not complete in time for any reason. Although the fallback scan prescription may have a time or radiation dose inefficiency compared to a fully optimized adaptive mCTA prescription, the fallback prescription ensures that the diagnostic image quality is not compromised by stopping the scan too early when the scan prescription is not successfully adapted.

At 1114, method 1100 optionally includes positioning/identifying a monitoring region of interest (ROI) for contrast monitoring. The monitoring ROI may comprise a specific region of the patient wherein contrast level is monitored during the scan. In some examples, the monitoring ROI may be positioned outside of the area of the patient to be imaged. In other examples, the monitoring ROI may be positioned within the imaging area such that the projection data acquired for diagnostic purposes may also be used for monitoring. Thus, an operator may select the monitoring ROI based on the preliminary or baseline image acquired at 1106 or 1108. Determining the monitoring ROI may therefore comprise receiving a selection of a monitoring ROI from the operator, for example, via operator console 220 of FIG. 2. In some examples, the monitoring ROI may be not be identified/positioned. Rather, the monitoring ROI may be segmented tissue from a plurality of reconstructed images (e.g., when the tissue uptake curve signal is used to estimate the AIF/VOF curves and/or time points of interest).

At 1116, an injection of contrast agent into the patient is performed. For example, the injection may be a contrast bolus, and the mCTA described herein may be performed in-flight with the contrast level measurement (e.g., where smart prep is used). As another example, the injection may be a timing bolus, such as described above with respect to FIG. 3, and a subsequent (e.g., second) injection may be used for the mCTA. As a non-limiting example, the contrast agent may comprise iodine. As other examples, the contrast agent may comprise an ionic contrast medium, such as meglucamine diatriozoate, or a non-ionic contrast medium, such as iopromide or ohexol. The contrast agent may be intravenously injected using either automatic or manual methods.

At 1118, an AIF or TUC signal is measured upon (e.g., immediately after or concurrent with) the first injection. In some examples, such as where smart prep is used, the measurement may be a first pass (e.g., phase) of the mCTA. Because the mCTA may be updated in-flight, the AIF signal may not necessarily be the full AIF curve. Rather, the AIF signal may include measurement of a first segment of the AIF curve, e.g., to the arterial peak, as shown in FIG. 3. In such examples, the AIF signal may be measured until just after the arterial peak is reached. A rate of change in contrast level (e.g., an instantaneous rate of change or a slope of the AIF curve) may be monitored to determine when the arterial peak has been reached. For example, a positive rate of change indicates that the contrast level is increasing, while a negative rate of change indicates that the contrast level is decreasing. Once a negative rate of change is indicated for at least two successive samples (e.g., scan acquisitions) following a positive rate of change indication for at least two successive samples (e.g., scan acquisitions) during measurement of the AIF signal, it may be confirmed that the arterial peak has been reached. Likewise, if used (e.g., for a virtual mCTA-from-CTP), the TUC signal may include a measurement of a first segment of the TUC until the tissue uptake peak, as shown in FIG. 4. For the TUC signal, once a negative rate of change is indicated for at least two successive samples (e.g., scan acquisitions) following a positive rate of change for at least two successive samples during measurement of the TUC signal, it may be confirmed that the tissue uptake peak has been reached.

To measure the AIF signal or the TUC signal, a plurality of images of the monitoring ROI (e.g., an artery) or tissue of interest (e.g., brain) may be reconstructed (e.g., by image reconstructor 230 of FIG. 2) from projection data obtained by the CT system (e.g., from projection data obtained via detector array 108, which detects x-rays generated by x-ray source 104 of FIG. 1) with a relatively low x-ray dose (e.g., a tube current of 50 mA or less). The signal intensity (e.g., in HU) of the monitoring ROI or segmented tissue relative to a baseline level for each image may be determined and plotted as a function of time to arrive at the AIF signal or TUC signal.

At 1120, method 1100 includes displaying a notification of the scan progress via the run-time GUI. For example, the run-time GUI may include a visual indicator of the scan progress that may change as the scan progresses. The visual indicator may include one or more progress bars, which may indicate scan progression by progressively changing in color or brightness over time (e.g., from left to right across the progress bar), and may include relative timing of each acquisition and a time between each acquisition. Additional details about the run-time GUI are provided below with respect to FIG. 20.

At 1122, method 1100 includes determining the marker from the AIF or TUC signal. As one example, the marker may be an arterial peak time (e.g., a time until the arterial peak) tAp, as described above with respect to FIG. 3, which may be calculated from the smart prep or directly determined using the smart prep or the timing bolus. As another example, the marker may be a smart prep trigger time (tSPt), which may be equivalent to an x-ray on time for the mCTA first pass. In some examples, tAp may be used to predict a time of the venous return to baseline (tVRTB). In such examples, the marker may be the predicted tVRTB. As still another example, the marker may be a TUC peak time (e.g., point V on the TUC 406 of FIG. 4) or may be derived from the TUC peak time. For example, when the TUC signal is obtained and not the AIF, the computing device may approximate tAp as a function of the TUC through the TUC peak time using a closed form calculus-based relationship stored in memory.

At 1124, method 1100 includes generating a personalized mCTA scan prescription based on the marker. As one example, the computing device may input the marker into an adaptive mCTA scan prescription lookup table associated with the selected adaptive mCTA scan protocol that is stored in memory, and the adaptive mCTA scan prescription lookup table may output a number of mCTA passes to perform and/or an amount of time between each pass for the input marker. Example adaptive mCTA scan prescription lookup tables are shown in FIGS. 12 and 13, as will be described below. Further, at least some of the parameters in the adaptive mCTA scan prescription lookup table may be adjustable by the lead technician and/or the operator within pre-programmed scan constraints using the adaptive scan protocol GUI, as elaborated above with respect to FIGS. 7-10. Further still, the computing device may store a plurality of different adaptive mCTA scan prescription lookup tables in memory, and the selected scan protocol (e.g., as selected at 1104) may determine which lookup table is used to update the mCTA scan protocol.

Further, the generated personalized mCTA scan prescription does not exclude the parameter settings given in the fallback prescription. For example, when the marker is relatively long (e.g., the arterial peak time is relatively late), it may be optimal to perform the maximum number of mCTA phases. Thus, it may be understood that the generated personalized mCTA scan prescription for some patients may include the same number of passes and/or the same amount of time between each pass as the fallback prescription.

Turning briefly to FIG. 12, a first example adaptive mCTA scan prescription lookup table 1200 is shown. The adaptive mCTA scan prescription lookup table 1200 includes a group of columns 1202 defining a marker and a marker range and a column 1204 defining a number of mCTA scan passes. Each row defines the number of mCTA scan passes to prescribe for each corresponding marker range. Underlined text corresponds to values that may be adjusted.

In the example shown, the selected marker is the tSPt. Therefore, the computing device may input the tSPt into the adaptive mCTA scan prescription lookup table 1200, which may output the corresponding number of passes for the input tSPt. In the example shown, if the tSPt is less than or equal to 20 seconds, the generated personalized mCTA scan prescription will include three scan passes, as shown in a first row 1206. If the tSPt is greater than 20 second and less than or equal to 30 seconds, the generated personalized mCTA scan prescription will include four scan passes, as shown in a second row 1208. If the tSPt is greater than 30 seconds and less than or equal to 40 seconds, the generated personalized mCTA scan prescription will include five scan passes, as shown in a third row 1210. If the tSPt is greater than 40 seconds, the generated personalized mCTA scan prescription will include six scan passes, as shown in a fourth row 1212.

Continuing to FIG. 13, a second example adaptive mCTA scan prescription lookup table 1300 is shown. The adaptive mCTA scan prescription lookup table 1300 includes a group of columns 1302 defining a marker and a marker range, a column 1304 defining a minimum number of passes, a column 1306 defining a maximum amount of time between passes, and a column 1308 defining a minimum amount of time between the first pass and the last pass. Each row defines the number of mCTA scan passes to prescribe for each corresponding marker range. Underlined text corresponds to values that may be adjusted.

In the example shown, the selected marker is an x-ray on-time for the first pass. Therefore, the computing device may input the x-ray on time for the first pass into the adaptive mCTA scan prescription lookup table 1300, which may output the corresponding number of passes to prescribe for the input time. In the example shown, if the x-ray on time for the first pass is less than or equal to 20 seconds, a minimum of three scan passes will be prescribed with a maximum of 8 seconds between each pass and a minimum of 15 seconds between the first pass and the last pass, as shown in a first row 1310. If the x-ray on time for the first pass is greater than 20 second and less than or equal to 30 seconds, a minimum of four scan passes will be prescribed with a maximum of 9 seconds between each pass and a minimum of 26 seconds between the first pass and the last pass, as shown in a second row 1312. If the x-ray on time for the first pass is greater than 30 seconds and less than or equal to 40 seconds, a minimum of five scan passes will be prescribed with a maximum of 10 seconds between each pass and a minimum of 39 seconds between the first pass and the last pass, as shown in a third row 1314. If the x-ray on time for the first pass is greater than 40 seconds, a minimum of six scan passes will be prescribed with a maximum of 11 seconds between each pass and a minimum of 54 seconds between the first pass and the last pass, as shown in a fourth row 1316.

Returning to 1124, as another example, additionally or alternatively, the computing device may input the marker into a trim lookup table to determine a number of passes to trim from the maximum number of passes described above at 1112. The computing device may store a plurality of different trim lookup tables in memory, and the selected protocol may determine which trim lookup table is used to generate the personalized mCTA scan prescription. In some examples, the computing device may input the marker into both an adaptive mCTA scan prescription lookup table and a trim lookup table to determine, for example, the number of mCTA passes, a timing between each pass, and/or a total scan time for the generated personalized mCTA scan prescription. An example workflow for utilizing a trim lookup table will be described below with respect to FIG. 15. Further, example trim lookup tables and corresponding adaptive mCTA scan prescription lookup tables will be described with respect to FIGS. 16 and 17.

Whether an adaptive mCTA scan prescription lookup table and/or a trim lookup table is used, in general, the generated personalized mCTA scan prescription may include a larger number of passes when the marker is larger (e.g., it takes more time to reach tAp). As another example, as the marker increases, the amount of time between each pass and/or the total scan time may increase. Because a goal of the mCTA scan is to acquire passes from the arterial peak though the end of the venous decent (e.g., the venous return to baseline) in order to assess collateral blood flow to the infarcted area, extending the scan by increasing the number of passes and/or increasing the total scan time when the marker is longer in duration may increase a likelihood that the end of the venous decent is imaged, while reducing the number of passes and/or decreasing the total scan time when the marker is shorter in duration may decrease the radiation dose and decrease an amount of time before a diagnosis can be made while still capturing the venous decent.

At 1126, method 1100 includes displaying confirmation of the generated personalized mCTA scan prescription via the run-time GUI. For example, after the scan prescription is generated and/or adjusted, a visual representation of the scan prescription may be displayed as part of the run-time GUI, with the visual representation showing an example AIF curve, TUC, and/or VOF curve and with the timing of individual acquisitions as dictated by the scan prescription shown as part of the curve.

At 1128, method 1100 includes performing the mCTA scan. For example, the mCTA scan is carried out with acquisition phases (e.g., passes) that are timed based on the marker according to the generated personalized mCTA scan prescription determined at 1124. Alternatively, if the mCTA scan protocol cannot be updated, the maximum number of mCTA phases may be performed. Performing the mCTA scan may include performing a first acquisition at the estimated arterial peak timing and performing the prescribed number of subsequent acquisitions at fixed or variable timings relative to the first acquisition and depending on the generated personalized mCTA scan prescription. In some examples, each of acquisitions may be of the same anatomical area. In other examples, at least some of the acquisitions may be in different anatomical areas. For example, the first acquisition may be of the head and neck while additional acquisitions may be of the head only. In some examples, each acquisition may be performed with the same scan parameters (e.g., same tube current, same tube voltage, etc.). In other examples, one or more of the acquisitions may be performed with different scan parameters (e.g., the first acquisition may be performed with a first, higher tube current and second and third acquisitions may be performed with a second, lower tube current).

At 1130, method 1100 includes displaying a notification once the scan is complete via the run-time GUI. Thus, the operator may be informed that the scan is complete.

At 1132, one or more diagnostic images are reconstructed based on data acquired during the mCTA scan. For example, one or more diagnostic images may be reconstructed using known reconstruction techniques, such as filtered back projection or iterative reconstruction. The one or more diagnostic images may be output to a display device (e.g., display device 232 of FIG. 2) for display to an operator or a physician, to a storage medium (e.g., mass storage 218 of FIG. 2) for retrieving at a later time, and so on. Method 1100 may then end.

Thus, method 1100 provides for a personalized mCTA scan that may be tailored to patient-specific physiology without prior knowledge regarding the patient age and hemodynamics. Using the contrast signal (e.g., the AIF or TUC signal) that is measured prior to or during the first acquisition of the mCTA, the acquisitions of the mCTA may be timed to better capture the VRTB without using complex algorithms and machine learning models, for example. The personalized mCTA scan described herein may be applied to create a streamlined/automated workflow that automatically computes/updates the entire adaptive mCTA prescription based on the measured marker. In doing so, a cognitive load on the user (e.g., scan technologist) may be decreased, as the user does not have to determine if a fourth acquisition is needed, for example. Further, variances in scan protocols between users, as well as the diagnostic quality of the scans performed, may be decreased. In other examples, the workflow may be semi-automatic, where the system suggests an update to the mCTA prescription (based on the patient physiology) to the user relative to a fallback mCTA protocol and the user has the opportunity to select or reject the updated prescription on-the-fly.

Next, FIG. 14 shows a set of plots 1400 including example adaptive mCTA scans for two example patients. For example, the personalized scan prescription for each example patient may be determined via the method of FIG. 11. In particular, the example shown uses an adaptive mCTA scan protocol that adjusts the prescribed number of acquisition phases based on tAp while maintaining an amount of time between each phase constant. A first plot 1401 shows an AIF curve 1402 and a VOF curve 1404 for a first patient (e.g., in HU as a function of time). A first time point 1405 corresponds to when a first mCTA acquisition is performed for the first patient. The first acquisition may be performed at the arterial peak for the first patient (point B on the AIF curve). Based on the arterial peak time of the first patient (tAp1), which occurs between a time point t1 (e.g., when a contrast agent is injected) and point B on the first plot 1401, the adaptive mCTA scan protocol prescribes three acquisition phases for the first patient. A second time point 1407 corresponds to when a second mCTA acquisition phase is performed for the first patient. In the example shown, the second acquisition phase is performed at a fixed time after the arterial peak, herein at 8 seconds after the arterial peak, although in other examples, the time may vary. A third time point 1409 corresponds to when a third mCTA acquisition phase is performed for the first patient. The third acquisition phase is performed at a fixed time after the arterial peak, herein at 16 seconds after the arterial peak (e.g., 8 seconds after the second phase).

A second plot 1410 shows an AIF curve 1412 and a VOF curve 1414 for a second patient (e.g., in HU as a function of time). The second patient has a longer venous decent than the first patient. For example, the second patient may be 80 years old or older and/or the second patient may have atrial fibrillation, although this may be unknown to the scan operator. A first time point 1415 corresponds to when a first mCTA acquisition phase is performed for the second patient. The first acquisition performed may be performed at the arterial peak for the second patient (point B on the AIF curve of the second plot 1410). Based on the arterial peak time of the second patient (tAp2), which occurs between time point t1 and point B of the second plot 1410 and is greater than tAp1 of the first patient, the adaptive mCTA scan protocol prescribes four acquisition phases for the second patient. A second time point 1417 corresponds to when a second mCTA acquisition phase is performed for the second patient. In the example shown, the second acquisition is performed at a fixed time after the arterial peak, herein at 8 seconds after the arterial peak. A third time point 1419 corresponds to when a third mCTA acquisition is performed for the second patient. The third acquisition is performed at a fixed time after the arterial peak, herein at 16 seconds after the arterial peak (e.g., 8 seconds after the second acquisition phase). A fourth time point 1421 corresponds to when a fourth mCTA acquisition is performed for the second patient. The fourth acquisition may be performed at a fixed time after the arterial peak, herein at 24 seconds after the arterial peak (e.g., 8 seconds after the third acquisition phase).

Thus, using the same adaptive mCTA scan protocol results in individualized prescriptions for the two patients. As a result, the final acquisition of each scan is performed as the VOF curve returns to baseline, and the obtained images may be suitable for determining a diagnosis for each patient without unnecessarily prolonging the scan for the first patient or prematurely ending the scan for the second patient.

Figure 15:
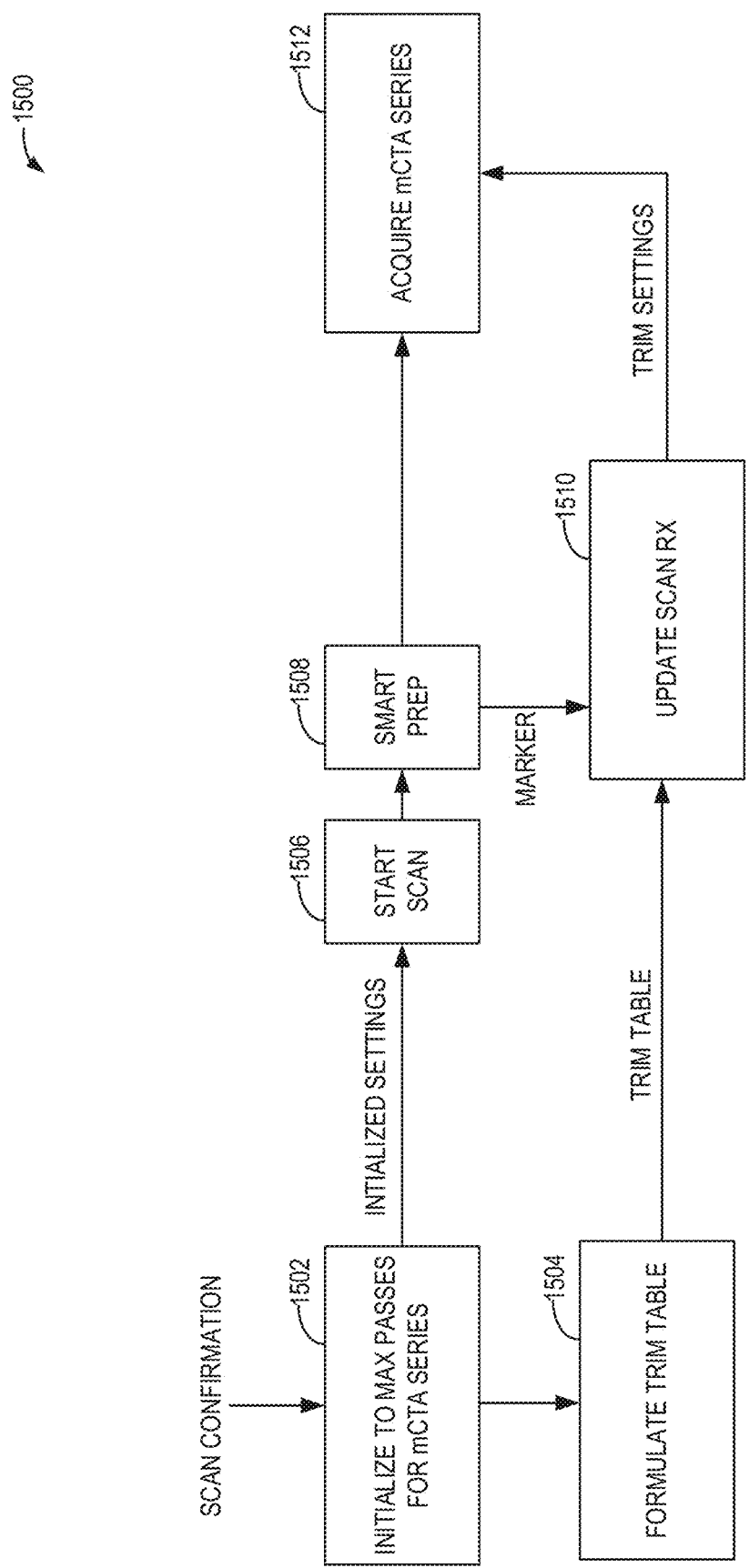
FIG. 15 shows an example workflow for trimming scan acquisition phases from a fallback prescription in-flight, according to an embodiment of the disclosure.

Turning now to FIG. 15, an example workflow 1500 is shown for initializing an adaptive mCTA scan to a fallback prescription and updating the scan prescription in-flight by trimming passes that are not intended. As one example, the workflow 1500 may be incorporated into method 1100 of FIG. 11 (e.g., at 1112 and 1124). Further, the workflow 1500 may be executed via a computing device (e.g., the computing device 216 of FIG. 2) based on instructions stored in non-transitory memory of the computing device in order to operate a CT system, such as the CT system of FIGS. 1-2. Further, although the workflow 1500 is described with respect to an mCTA scan, variants of the workflow 1500 may be applied to other contrast scans that may be adjusted in-flight based on measured/estimated patient parameters.

Upon receiving an indication of an mCTA scan confirmation from an operator of (e.g., via a run-time GUI), at 1502, the workflow 1500 includes initializing to a maximum number of passes that may be used for the mCTA series (e.g., the fallback prescription). As described above with respect to 1112, the maximum number of passes may be a predetermined value stored in memory and may correspond to a highest number of passes to perform during any mCTA scan based on time and radiation dosage constraints while maintaining diagnostic image quality. Further, in some examples, the fallback prescription may include a smallest amount of time between each pass (e.g., tau), and the system may be initialized to this time value (e.g., 8 seconds).

Upon initializing the CT system, the workflow 1500 formulates a trim table at 1504, examples of which will be described with respect to FIGS. 16 and 17. The trim table dictates how many passes to trim from the maximum number of passes given a measured/estimated patient marker (e.g., tAp) that is determined during the scan. As one example, the maximum number of passes is 6. As another example, the maximum number of passes is 7. The workflow 1500 also uses the initialized settings to start the scan at 1506. For example, starting the scan may include administering contrast agent to the patient and measuring an AIF signal. Further, in starting the scan, the workflow 1500 may transmit a message to the CT system indicating the number of prescribed passes (e.g., nPasses), which is set to the maximum number. The workflow 1500 may further transmit a message regarding the number of passes to trim from the scan (e.g., nTrim) and the number of passes to trim currently (e.g., trimNow). Because the patient marker has not yet been identified, both nTrim and trimNow are set to zero in starting the scan.

In the example shown, at 1508, the workflow 1500 includes using smart prep to identify the marker, although in other examples, a timing bolus may be used. As described above with respect to FIG. 3, smart prep may refer to an in-flight AIF measurement that occurs using the same contrast agent bolus that is administered for the contrast scan. By measuring the AIF curve, the system may identify the patient marker, which may be an arterial peak time (tAp), a smart prep trigger time (tSPt), or the like.

The workflow 1500 inputs both the identified patient marker and the trim table to update the scan prescription at 1510. In some examples, the trim table may determine a number of passes to trim from the fallback prescription based on the patient marker, which may be used to update the scan prescription at 1510. In other examples, the trim table may determine a minimum number of passes to trim from the fallback prescription and a maximum number of passes to trim from the fallback prescription based on the patient marker, and the system may use this information to adjust both the timing and number of passes by updating the scan prescription at 1510. Further, in some examples, the trim table may relate the patient marker to a maximum tau value in addition to the number of passes, and the maximum tau value may be further used to update the scan prescription at 1510.

The updated scan prescription may be used to acquire the mCTA series at 1512. As one example, the workflow 1500 may transmit a message regarding the total number of passes to trim (nTrim) and the number to currently trim (trimNow). The number to currently trim may be 1, for example, even when nTrim is greater than one, so that if the next to last pass is already underway when the nTrim message is received, a best possible action is performed (e.g., trimming the final pass). As another example, the workflow 1500 may transmit a message regarding the minimum number of passes to trim from the scan (e.g., nTrimU1), the maximum number of passes to trim from the scan (e.g., nTrimU2), the desired tau, and the number to currently trim. The maximum number of passes to trim from the scan may correspond to the number of passes to trim if tau is able to be updated before the second pass, whereas the minimum number of passes to trim from the scan may correspond to the number to passes to trim if tau cannot be updated before the second pass. The system may acquire the mCTA series by triggering acquisitions at the determined timings for the number of passes indicated by the updated scan prescription 1510, if able, or may use the fallback scan prescription if unable to update the scan prescription.

Figure 16:
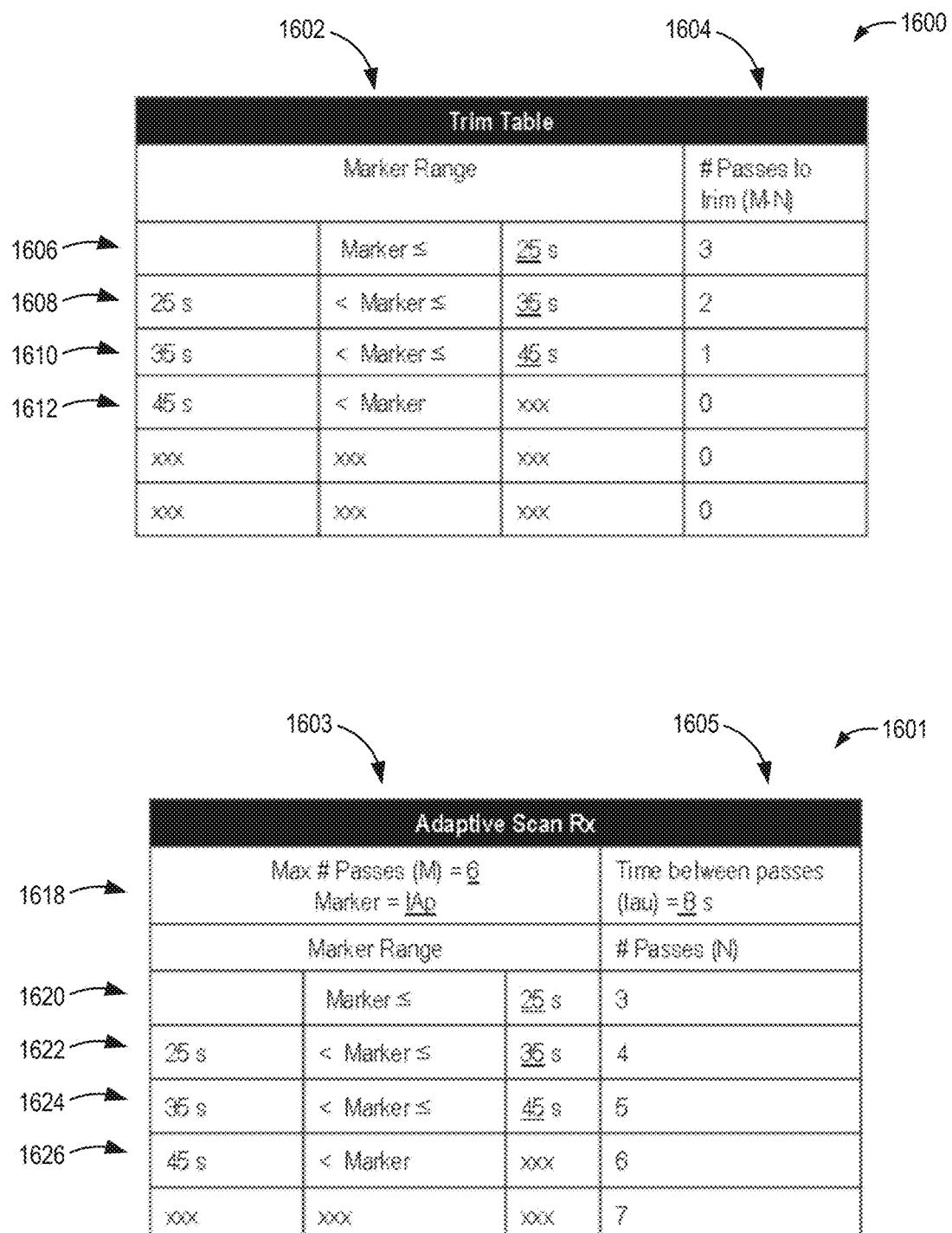
FIG. 16 shows a first example trim table and corresponding scan prescription lookup table that may be used in the workflow of FIG. 15.

Continuing to FIG. 16, a first example trim table 1600 and a corresponding adaptive scan prescription lookup table 1601 are shown. For example, the trim table 1600 may be formulated at 1504 of the workflow 1500 of FIG. 15, and the adaptive scan prescription lookup table 1601 may be formulated based on the trim table 1600 and used at 1510 of workflow 1500. In both the trim table 1600 and the adaptive scan prescription lookup table 1601, underlined text indicates text that may be modified. Further, values may be linked between the two tables, as will be elaborated below.

The trim table 1600 includes a group of columns 1602 indicating a marker range and a column 1604 indicating a number of passes to trim from a maximum number of passes (M). The resulting number of passes to trim is equal to the maximum number of passes minus a number of passes that will be used for the scan (N). The adaptive scan prescription lookup table 1601 includes a group of columns 1603 indicating the marker range and a column 1605 indicating the number of passes that will be used for the scan. Further, the adaptive scan prescription lookup table 1601 includes a parameter row 1618 where M, the marker, and tau are set. In the example shown, M is set to 6 passes, the marker is set to tAp, and tau is set to 8 seconds. Thus, both the trim table 1600 and the adaptive scan prescription lookup table 1601 will use tAp as the marker and time the passes such that 8 seconds elapse between each pass.

A first row 1606 of trim table 1600 indicates that 3 passes will be trimmed when the marker is less than or equal to 25 seconds. Because 3 passes will be trimmed from the maximum number of 6 passes, a corresponding first row 1620 of the adaptive scan prescription lookup table 1601 indicates that 3 passes will be used when the marker is less than or equal to 25 seconds. If the marker range were to be adjusted in the first row 1606, the marker range would also be adjusted in the first row 1620 (and vice versa). For example, adjusting 25 seconds to 20 seconds in the first row 1606 would result in the parameter in the first row 1620 changing to 20 seconds. A second row 1608 of trim table 1600 indicates that 2 passes will be trimmed when the marker is greater than 25 seconds and less than or equal to 35 seconds. Because 2 passes will be trimmed from the maximum number of 6 passes, a corresponding second row 1622 of the adaptive scan prescription lookup table 1601 indicates that 4 passes will be used when the marker is greater than 25 seconds and less than or equal to 35 seconds. A third row 1610 of trim table 1600 indicates that 1 pass will be trimmed when the marker is greater than 35 seconds and less than or equal to 45 seconds. Because 1 pass will be trimmed from the maximum number of 6 passes, a corresponding third row 1624 of the adaptive scan prescription lookup table 1601 indicates that 5 passes will be used when the marker is greater than 35 seconds and less than or equal to 45 seconds. A fourth row 1612 of trim table 1600 indicates that 0 passes will be trimmed when the marker is greater than 45. Because no passes will be trimmed from the maximum number of 6 passes, a corresponding fourth row 1626 of the adaptive scan prescription lookup table 1601 indicates that 6 passes will be used when the marker is greater than 45 seconds. The trim table 1600 and the adaptive scan prescription lookup table 1601 both include one or more additional rows that are not populated because no less than 0 passes may be trimmed from the scan, but in other examples (e.g., when the parameter row 1618 includes different values), the additional rows may be populated. Thus, the number of populated rows shown in each table in FIG. 16 is illustrative.

As an illustrative example, the tAp of a first patient is determined to be 29 seconds. According to the second row 1608 of the trim table 1600, 2 passes should be trimmed from the fallback prescription. Thus, the adaptive scan prescription lookup table 1601 prescribes 4 passes for the first patient in the second row 1622. As another illustrative example, the tAp of a second patient is determined to be 45 seconds. According to the third row 1610 of the trim table 1600, 1 pass should be trimmed from the fallback prescription of 6 passes. Thus, the third row 1624 of the adaptive scan prescription lookup table 1601 prescribes 5 passes for the second patient.

Figure 17:
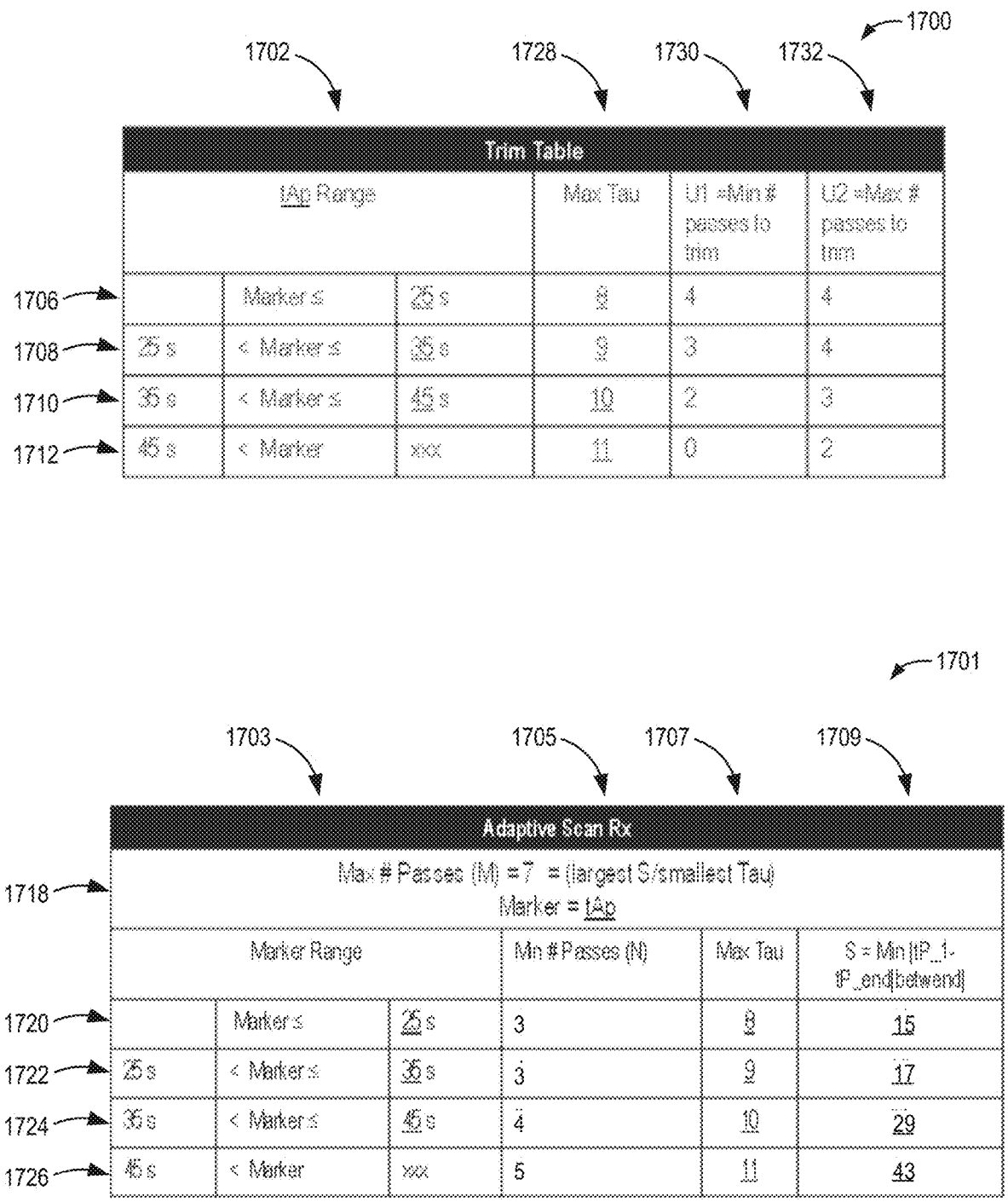
FIG. 17 shows a second example trim table and corresponding scan prescription lookup table that may be used in the workflow of FIG. 15.

FIG. 17 shows a second example trim table 1700 and a corresponding adaptive scan prescription lookup table 1701. For example, the trim table 1700 may be formulated at 1504 of the workflow 1500 of FIG. 15, and the adaptive scan prescription lookup table 1701 may be formulated based on the trim table 1700 and used at 1510 of workflow 1500. In both the trim table 1700 and the adaptive scan prescription lookup table 1701, underlined text indicates text that may be modified. Further, values may be linked between the two tables, as will be elaborated below.

The trim table 1700 includes a group of columns 1702 indicating a marker range, a column 1728 indicating a maximum tau, a column 1730 indicating a minimum number of passes to trim (U1) from a maximum number of passes (M), and a column 1732 indicating a maximum number of passes to trim (U2) from the maximum number of passes.

The adaptive scan prescription lookup table 1701 includes a group of columns 1703 indicating the marker range, a column 1705 indicating a minimum number of passes that will be used for the scan, a column 1707 indicating a maximum tau value, and a column 1709 indicating a minimum amount of time between a first pass of the scan and a last pass of the scan (S). Further, the adaptive scan prescription lookup table 1701 includes a parameter row 1718 where M and the marker are set. In the example shown, M is set to 7 passes and the marker is set to tAp. Further, M is defined as the largest S divided by the smallest tau, meaning that the maximum number of passes is equal to the greatest number of passes that can be performed within a longest desired total scan time. Thus, both the trim table 1700 and the adaptive scan prescription lookup table 1701 will use tAp as the marker and time the passes such that a variable amount of elapses between each pass, with tau increasing as tAp increases. In the example shown, tau increases by 1 second increments, although other increments may also be used (e.g., 2 seconds).

A first row 1706 of trim table 1700 indicates that when the marker is less than or equal to 25 seconds, the maximum tau is 8 seconds, the minimum number of passes to trim is 4, and the maximum number of passes to trim is 4. Because 4 passes will be trimmed from the maximum number of 7 passes, a corresponding first row 1720 of the adaptive scan prescription lookup table 1701 indicates that 3 passes will be used when the marker is less than or equal to 25 seconds, with a minimum amount of time between the first pass and the last pass equaling 15 seconds (e.g., when less than the maximum tau of 8 seconds is used). If the marker range were to be adjusted in the first row 1706, the marker range would also be adjusted in the first row 1720 (and vice versa). For example, adjusting 25 seconds to 20 seconds in the first row 1706 would result in the parameter in the first row 1720 changing to 20 seconds. A second row 1708 of trim table 1700 indicates that when the marker is greater than 25 seconds and less than or equal to 35 seconds, the maximum tau is 9 seconds, the minimum number of passes to trim is 3, and the maximum number of passes to trim is 4. Because no more than 4 passes will be trimmed from the maximum number of 7 passes, a corresponding second row 1722 of the adaptive scan prescription lookup table 1701 indicates that a minimum of 3 passes will be used when the marker is greater than 25 seconds and less than or equal to 35 seconds, with the maximum tau of 9 seconds resulting in an S value of 17 seconds. A third row 1710 of trim table 1700 indicates that when the marker is greater than 35 seconds and less than or equal to 45 seconds, the maximum tau is 10 seconds, the minimum number of passes to trim is 2, and the maximum number of passes to trim is 3. Because no more than 3 passes will be trimmed from the maximum number of 7 passes, a corresponding third row 1724 of the adaptive scan prescription lookup table 1701 indicates that no fewer than 4 passes will be used when the marker is greater than 35 seconds and less than or equal to 45 seconds, with the maximum tau of 10 seconds resulting in an S value of 29 seconds. A fourth row 1712 of trim table 1700 indicates that when the marker is greater than 45 seconds, the maximum tau is 11 seconds, the minimum number of passes to trim is 0, and the maximum number of passes to trim is 2. Because no more than 2 passes will be trimmed from the maximum number of 7 passes, a corresponding fourth row 1726 of the adaptive scan prescription lookup table 1701 indicates that at least 5 passes will be used when the marker is greater than 45 seconds, with the maximum tau of 11 seconds resulting in an S value of 43 seconds. The trim table 1700 and the adaptive scan prescription lookup table 1701 may also include one or more additional rows that based on the values set in the parameter row 1718, and the values shown in each table of FIG. 17 are illustrative.

As an illustrative example, the tAp of a first patient is determined to be 29 seconds. According to the second row 1708 of the trim table 1700, no less than 3 and no more than 4 passes should be trimmed from the fallback prescription. Thus, the adaptive scan prescription lookup table 1701 prescribes a minimum of 3 passes for the first patient in the second row 1722, with a maximum of 9 seconds between each pass. As another illustrative example, the tAp of a second patient is determined to be 45 seconds. According to the third row 1710 of the trim table 1700, no less than 2 and no more than 3 passes should be trimmed from the fallback prescription of 7 passes. Thus, the third row 1724 of the adaptive scan prescription lookup table 1701 prescribes a minimum of 4 passes for the second patient, with a maximum of 10 seconds elapsing between each pass.

Referring now to FIGS. 18 and 19, examples of initializing an mCTA scan to a fallback prescription and using a trim table to adapt the prescription in-flight is shown with respect to two example patients. In the examples shown, the fallback prescription includes 6 mCTA phases with a fixed tau value of 8 seconds between each phase. Turning first to FIG. 18, a set of plots 1800 includes a first plot 1801 corresponding to performing the mCTA scan of a first patient with the fallback prescription and a second plot 1810 corresponding to performing the mCTA scan of the first patient with the adapted prescription. Both the first plot 1801 and the second plot 1810 show an AIF curve 1802 and a VOF curve 1804 for the first patient (e.g., in HU as a function of time). A first time point 1815 corresponds to when a first mCTA acquisition is performed for the first patient. The first acquisition may be performed at the arterial peak for the first patient (point B on the AIF curve). The arterial peak time of the first patient (tAp1), which occurs between a time point t1 (when a contrast agent is injected) and point B, may be 40 seconds, for example, and may be input into the trim table 1600 of FIG. 16. Based on the arterial peak time of the first patient, the trim table indicates that one phase should be trimmed from the fallback prescription for the first patient.

In the first plot 1801, the prescription is unable to be updated, resulting in a second mCTA acquisition phase being performed at a second time point 1817, a third mCTA acquisition phase being performed at a third time point 1819, a fourth mCTA acquisition phase being performed at a fourth time point 1821, a fifth mCTA acquisition phase being performed at a fifth time point 1823, and a sixth mCTA acquisition phase being performed at a sixth time point 1825. Thus, the fallback prescription is performed, with the maximum number of acquisitions performed and 40 seconds elapsing between the first acquisition and the final acquisition. In contrast, the prescription is successfully updated in the second plot 1810, resulting in the sixth mCTA acquisition phase not being performed (e.g., the sixth time point 1825 is omitted). As a result, only 32 seconds elapse between the first acquisition and the final acquisition. Although both the first plot 1801 and the second plot 1810 may result in obtaining images with high diagnostic quality, by trimming the sixth mCTA acquisition phase, the diagnostic result may be received more quickly and a radiation dose of the mCTA scan may be reduced.

Continuing to FIG. 19, a set of plots 1900 includes a first plot 1901 corresponding to performing the mCTA scan of a second patient with the fallback prescription and a second plot 1910 corresponding to performing the mCTA scan of the first patient with the adapted prescription. Both the first plot 1901 and the second plot 1910 show an AIF curve 1902 and a VOF curve 1904 for the second patient (e.g., in HU as a function of time). A first time point 1905 corresponds to when a first mCTA acquisition is performed for the second patient. The first acquisition may be performed at the arterial peak for the first patient (point B on the AIF curve). The arterial peak time of the second patient (tAp2), which occurs between a time point t1 (e.g., when a contrast agent is injected) and point B, may be 20 seconds, for example, and may be input into the trim table 1600 of FIG. 16. Based on the arterial peak time of the first patient, the trim table indicates that three phases should be trimmed from the fallback prescription for the second patient.

In the first plot 1901, the prescription is unable to be updated, resulting in a second mCTA acquisition phase being performed at a second time point 1907, a third mCTA acquisition phase being performed at a third time point 1909, a fourth mCTA acquisition phase being performed at a fourth time point 1911, a fifth mCTA acquisition phase being performed at a firth time point 1912, and a sixth mCTA acquisition phase being performed at a sixth time point 1915. Thus, the fallback prescription is performed, with the maximum number of acquisitions performed and 40 seconds elapsing between the first acquisition and the final acquisition. In contrast, the prescription is successfully updated in the second plot 1910, resulting in the final three mCTA acquisition phases not being performed (e.g., the fourth time point 1911, the fifth time point 1913, and the sixth time point 1915 are omitted). As a result, only 16 seconds elapse between the first acquisition and the final acquisition. Although both the first plot 1901 and the second plot 1910 may result in obtaining images with high diagnostic quality, by trimming the final three mCTA acquisition phases from the fallback prescription, the diagnostic result may be received more quickly and a radiation dose of the mCTA scan may be lowered.

FIG. 20 shows an example run-time GUI 2000 that may be displayed on a display device (e.g., the display device 232 of FIG. 2) in response to a user request to execute an existing adaptive scan protocol. The run-time GUI 2000 is a non-limiting example of the run-time GUI that is displayed as part of method 1100 of FIG. 11, for example.

Run-time GUI 2000 includes a quick settings section 2010. The quick settings section 2010 further includes an adaptive multi-phase CTA acquisition prescription section 2002, which may be a replicate of any of the GUI 700 of FIG. 7, the GUI 800 of FIG. 8, the GUI 900 of FIG. 9, or the GUI 1000 of FIG. 10, for example. Thus, the adaptive scan protocol GUI used to define a preset protocol may be displayed within the run-time GUI 2000 for additional adjustments at run-time, if desired. For example, the operator is given the opportunity to confirm the settings for the current adaptive scan protocol, and if desired, change the settings to ensure that sufficient acquisitions are taken to capture the patient's venous return to baseline. The adaptive multi-phase CTA acquisition prescription section 2002 includes a preview section 2004, a prescription overview section 2006, and a detailed prescription section 2008, which may include any or all of the features described above with respect to FIGS. 7-10 and may function as previously described. As such, the scan prescription may be generated based on the selected adaptive scan protocol (e.g., fixed N, fixed T, minimize N, or minimize T).

While the preview section 2004 shown in FIG. 20 includes the same generic AIF curve, VOF curve, and TUC shown in the adaptive scan protocol GUIs described with respect to FIGS. 7-10, it is to be understood that at least in some examples, the run-time GUI 2000 may display a visual representation of the scan prescription that has been generated based on the patient's actual measured AIF signal, for example. As such, the preview section 2004 may be updated as patient-specific data become available. The patient-specific data may be obtained from a prior contrast scan, a timing bolus carried out before the current contrast scan, or during the current contrast scan. Thus, in some examples, during at least a first portion of the contrast scan, the generic AIF curve, VOF curve, and TUC may be displayed. In another example, the preview section 2004 may initially display a fallback scan prescription, which may be based on the fallback scan protocol as described above, and may not be based on patient information. Then, once the patient-specific data are generated, the fallback scan prescription may be replaced with the personalized curves.

The run-time GUI 2000 also includes a progress bar 2020 that displays the current status/progress of the contrast scan with respect to time. As the contrast scan progresses, the progress bar 2020 may change in visual appearance and/or update as the mCTA protocol is adjusted in-flight. For Additionally, the run-time GUI 2000 may include a patient information section 2030, a scan information section 2040, a scan range selection section 2050, an all settings section 2005, and a dose information section 2060. In the patient information section 2030, information about the imaging subject may be displayed, such as a patient name and/or ID number, patient gender, and patient position (e.g., head first/supine). In the scan information section 2040, information about the scan protocol may be displayed, such as the name of the scan protocol and the sequences of the scan protocol (e.g., the scout scan and contrast scan or scans, which includes an adaptive mCTA in the example shown in FIG. 20). Additionally, when a sequence of the scan protocol is completed, a checkmark or other visual indicator may be displayed. The current sequence may be highlighted or otherwise visually indicated. In the dose information section 2060, information about the x-ray radiation dose administered to the imaging subject may be displayed, such as projected dose, total accumulated dose, etc., so that the operator of the imaging system may monitor the patient's x-ray radiation exposure.

In the scan range selection section 2050, scout images of the imaging subject may be displayed with the current scan range displayed as an overlay of location markers on the scout image(s). As another example, when scout images are not available, the scan range may be displayed as an overlay on a generic image of a similar scan (e.g., same patient orientation) that is not specific to the imaging subject. The scan range may be adjusted by adjusting the location markers in the overlay. In particular, the location markers may define three scan locations, including a top of the head, a bottom of the head, and a bottom of the neck. The operator may adjust the location markers in a relative fashion such that when one of the three locations is adjusted, the other two locations are adjusted accordingly. As such, the operator may set an explicit location for the top of the head, and the locations for the bottom of the head and the bottom of the neck may be automatically set relative to the top of the head setting. For example, the bottom of the head location may be offset from the top of the head location by a first pre-determined distance, and the bottom of the neck location may be offset from the top of the head location by a second pre-determined distance. The first pre-determined distance and the second pre-determined distance may be pre-programmed by a lead technologist, for example, as described above with respect to FIGS. 5 and 6. As a result, the run-time GUI 2000 reduces a number of locations the operator defines at scan time, which may reduce a cognitive load on the operator and reduce an amount of time before diagnostic images of the patient are obtained.

In the all settings section 2005, the operator may define the start location of the scan, the end location of the scan, a range of the scan, a number of images to acquire, the anatomy being imaged, and other anatomy selection settings. The operator may further select settings related to a current and/or voltage of an x-ray source used, contrast settings, scan type settings, coverage speed settings, and reconstruction settings. The settings may be pre-filled based on a selected pre-defined protocol and/or adjusted by the operator at run-time.

Further, the run-time GUI 2000 may include one or more user interface inputs that, when selected by the operator, confirm the scan protocol setting and/or trigger the start of the contrast scan. In the example shown, the run-time GUI 2000 includes a confirm settings input 2065, which may trigger the start of the contrast scan. In some examples, the operator may not make adjustments to the scan settings (e.g., in the all settings section 2005 and the quick settings section 2010), enabling the operator to start the scan via the confirm settings input 2065 without performing additional protocol set-up. Thus, the run-time GUI 2000 enables the operator to begin the scan via a single selection of the confirm settings input 2065, if desired. As such, the run-time GUI 2000 provides a technical solution for reducing a cognitive load on the operator at scan time and reducing an amount of time before the scan is commenced. Further, the run-time GUI 2000 is shown including a done scanning input 2070, which may trigger the end of the contrast scan and save all acquired data and parameter settings to a unique file.

Thus, the systems and methods disclosed herein provide for personalizing a multi-phase mCTA scan for a specific patient without prior knowledge of the patient's information and hemodynamics, using (at least initially) a short measured segment (referred to as a contrast signal) of a contrast enhancement curve measured at a monitoring area. The contrast enhancement curve may be an arterial inflow function (AIF) curve, and the segment of the AIF curve may be measured at an artery of the patient, in an example. In another example, the contrast enhancement curve may be a tissue uptake curve (TUC), and the segment may be measured at a tissue of interest (e.g., the brain), where the tissue is segmented in a plurality of images. The AIF curve or the TUC may be used to determine a patient-specific marker, which serves as an identifiable event within a smart prep series or a timing bolus. The patient-specific marker may be an estimated or measured arterial peak time, a smart prep trigger time, or an x-ray on-time for a diagnostic scan immediately following smart prep, for example. The patient-specific marker may be used while the scan is in progress (e.g., in-flight) to update the mCTA scan prescription, including a number of scan phases to perform and/or an amount of time between each phase. Updating the scan prescription may include relating the patient-specific marker to the number of scan phases to perform and/or the amount of time between each phase via a lookup table. Additionally or alternatively, the patient-specific marker may be input into a trim table that outputs a number of phases to remove from a fallback prescription. The lookup table and the trim table may be defined by a protocol manager via one or more graphical user interfaces (GUIs), and a scan operator may further adjust the prescription via a run-time GUI, if desired.

As a result, the mCTA scan may be adapted to the patient's blow flow without machine learning or other computationally expensive models and without knowledge of the patient's history.

By including selectable pre-programmed adaptive scan protocols, a cognitive load on the scan operator may be reduced. As such, both intra-operator and inter-operator variability may be reduced, with a consistency of the scan quality and diagnostic information obtained for each patient increased. Further, an amount of time it takes to set up the scan may be reduced, which may decrease an amount of time it takes to reach a diagnosis and increase favorable patient outcomes. By adapting the mCTA scan to a patient-specific marker that is determined just prior to or during the diagnostic scan, a diagnostic image quality of the mCTA scan may be increased while a scan time and/or radiation dose may be decreased.

A technical effect of the disclosure is that an adaptive, personalized multi-phase angiography scan may be performed, which may increase diagnostic image quality and/or reduce patient radiation exposure. Another technical effect of the disclosure is that by initializing to a fallback prescription, a number of repeated scans may be reduced, which may reduce patient radiation exposure and increase positive patient outcomes. A further technical effect of the disclosure is that by selecting from pre-programmed adaptive protocols, a number of steps that an operator performs at scan time is reduced, which may decrease an amount of time before a diagnosis is made and increase positive patient outcomes.

In one embodiment, a method comprises processing acquired projection data of a monitoring area of a subject to measure a contrast signal of a contrast agent delivered to the subject; determining a hemodynamic marker of the subject based on the contrast signal; generating a scan prescription based on the determined hemodynamic marker of the subject; and performing a multi-phase contrast scan according to the scan prescription. In a first example of the method, the monitoring area is an artery and the contrast signal comprises at least a segment of an arterial inflow function (AIF) curve. In a second example of the method, which optionally includes the first example, the hemodynamic marker is a peak time of the AIF curve. In a third example of the method, which optionally includes one or both of the first and second examples, the hemodynamic marker is a venous return to baseline time that is estimated from a peak time of the AIF curve. In a fourth example of the method, which optionally includes any or all of the first through third examples, the monitoring area is a tissue of interest, the contrast signal comprises at least a segment of a tissue update curve (TUC), and the hemodynamic marker is a function of a peak time of the TUC. In a fifth example of the method, which optionally includes any or all of the first through fourth examples, generating the scan prescription based on the determined hemodynamic marker of the subject comprises determining at least one parameter of the multi-phase contrast scan via a plurality of pre-determined ranges that each relate a value to use for the at least one parameter when the determined hemodynamic marker is within a corresponding pre-determined range of the plurality of pre-determined ranges. In a sixth example of the method, which optionally includes any or all of the first through fifth examples, the plurality of pre-determined ranges are included in a lookup table, and determining the at least one parameter of the multi-phase contrast scan via the plurality of pre-determined ranges comprises inputting the determined hemodynamic marker of the subject into the lookup table. In a seventh example of the method, which optionally includes any or all of the first through sixth examples, the at least one parameter includes a number of acquisition phases to perform during the multi-phase contrast scan. In an eighth example of the method, which optionally includes any or all of the first through seventh examples, the at least one parameter includes an amount of time between each acquisition phase of the multi-phase contrast scan. In a ninth example of the method, which optionally includes any or all of the first through eighth examples, the scan prescription defines a number of acquisition phases and a timing of each acquisition phase to use for the multi-phase contrast scan, and performing the multi-phase contrast scan according to the scan prescription comprises acquiring projection data at the timing defined by the scan prescription for the number of acquisition phases defined by the scan prescription. In a tenth example of the method, which optionally includes any or all of the first through ninth examples, the contrast agent delivered to the subject is one of a timing bolus injection administered prior to performing the multi-phase contrast scan and a contrast agent bolus injection administered for performing the multi-phase contrast scan.

In another embodiment, a method for an imaging system comprises: processing acquired projection data of a monitoring area of a subject to measure a contrast signal of a contrast agent delivered to the subject via injection; generating a scan prescription for a contrast scan of the subject, including determining at least one of a number of acquisition phases to use for the contrast scan and an acquisition timing parameter of the contrast scan, based on the measured contrast signal; and performing the contrast scan with the imaging system according to the scan prescription. In a first example of the method, wherein generating the scan prescription for the contrast scan of the subject based on the measured contrast signal comprises: determining a hemodynamic marker of the subject based on the measured contrast signal; and inputting the hemodynamic marker of the subject into a lookup table that outputs at least one of the number of acquisition phases to use for the contrast scan and the acquisition timing parameter of the contrast scan for the input hemodynamic marker. In a second example of the method, which optionally includes the first example, the hemodynamic marker is determined based on a peak time of the measured contrast signal, and the measured contrast signal is one of an arterial inflow function curve, a venous outflow function curve, and a tissue uptake curve. In a third example of the method, which optionally includes one or both of the first and second examples, at least one of the number of acquisition phases to use for the contrast scan and the acquisition timing parameter of the contrast scan increases as a value of the hemodynamic maker increases. In a fourth example of the method, which optionally includes any or all of the first through third examples, the acquisition timing parameter includes at least one of an amount of time between a first of the number of acquisition phases and a last of the number of acquisition phases and an amount of time between each of the number of acquisition phases.

In another embodiment, a system comprises: an x-ray source that emits a beam of x-rays toward a subject to be imaged; a detector that receives the x-rays attenuated by the subject; a data acquisition system (DAS) operably connected to the detector; and a computer operably connected to the DAS and configured with instructions in non-transitory memory that when executed cause the computer to: process projection data of a monitoring region of interest (ROI) of the subject from the DAS to measure a contrast signal of a contrast agent injected into the subject; determine a hemodynamic marker of the subject based on the contrast signal, the hemodynamic marker used to approximate a duration between an arterial peak of the contrast agent at the monitoring ROI and a venous return to baseline of the contrast agent at the monitoring ROI; generate a scan prescription for a multi-phase contrast scan of the subject based on the hemodynamic marker of the subject; and perform the multi-phase contrast scan according to the scan prescription. In a first example of the system, the multi-phase contrast scan in a multi-phase angiography scan of an anatomy of interest selected from a plurality of possible anatomies of interest, the plurality of possible anatomies of interest including a head and a liver, and wherein the hemodynamic marker is determined immediately prior to or during a first acquisition of the multi-phase angiography scan. In a second example of the system, which optionally includes the first example, the anatomy of interest is the head, the first acquisition is of a head and neck of the subject, and each subsequent acquisition is only of the head of the subject. In a third example of the system, which optionally includes one or both of the first and second examples, the non-transitory memory stores a lookup table configured to determine at least one of a number of acquisition phases of the multi-phase contrast scan and a timing between each acquisition phase of the multi-phase contrast scan.

In another representation, a method for an imaging system comprises: initializing the imaging system to perform a plurality of acquisitions during a contrast scan according to a scan prescription; processing projection data obtained at an anatomical region of interest (ROI) of a subject to measure a contrast signal of a contrast agent administered to the subject; adjusting the scan prescription based on the measured contrast signal of the contrast agent; and performing the contrast scan according to the adjusted scan prescription. In a first example of the method, adjusting the scan prescription based on the measured contrast signal of the contrast agent comprises: determining a hemodynamic marker of the subject based on the measured contrast signal; and adjusting the scan prescription based on the hemodynamic marker. In a second example of the method, which optionally includes the first example, initializing the imaging system to perform the plurality of acquisitions during the contrast scan according to the scan prescription comprises initializing the imaging system to perform a pre-determined maximum number of acquisitions with a time duration between each acquisition set to a pre-determined minimum time duration. In a third example of the method, which optionally includes one or both of the first and second examples, adjusting the scan prescription based the hemodynamic marker comprises at least one of trimming a number of the acquisitions from the pre-determined maximum number of acquisitions and adjusting the time duration from the pre-determined minimum time duration based on the hemodynamic marker, with at least one of the number decreasing and the time duration increasing as the hemodynamic marker increases. In a fourth example of the method, which optionally includes any or all of the first through third examples, adjusting the scan prescription based on the hemodynamic marker comprises inputting the hemodynamic marker of the subject into a lookup table that outputs at least one of a number of acquisitions to trim from the pre-determined maximum number of acquisitions and an adjusted time duration. In a fifth example of the method, which optionally includes any or all of the first through fourth examples, the lookup table includes a plurality of marker ranges that each relate a set value to use for the number of acquisitions to trim from the pre-determined maximum number of acquisitions when the hemodynamic marker is within a corresponding marker range of the plurality of marker ranges. In a sixth example of the method, which optionally includes any or all of the first through fifth examples, the plurality of marker ranges each further relate a set time duration to use for the adjusted time duration when the hemodynamic marker is within the corresponding marker range. In a seventh example of the method, which optionally includes any or all of the first through sixth examples, the anatomical ROI is an artery and the contrast signal comprises at least a segment of an arterial inflow function (AIF) curve. In an eighth example of the method, which optionally includes any or all of the first through seventh examples, the hemodynamic marker is one of a peak time of the AIF curve and a venous return to baseline time that is estimated from a peak time of the AIF curve. In a ninth example of the method, which optionally includes any or all of the first through eighth examples, the anatomical ROI is a tissue of interest, the contrast signal comprises at least a segment of a tissue update curve (TUC), and the hemodynamic marker is a function of a peak time of the TUC. In a tenth example of the method, which optionally includes any or all of the first through ninth examples, the contrast agent is administered to the subject via one of a timing bolus injection administered prior to performing the contrast scan and a contrast agent bolus administered to initiate the contrast scan.

In yet another representation, a method for an imaging system comprises: initializing the imaging system to perform a multi-phase contrast scan of a subject according to a pre-determined scan prescription; processing acquired projection data of a monitoring area of the subject to measure a contrast signal of a contrast agent delivered to the subject; generating an updated scan prescription for performing the multi-phase contrast scan of the subject, including adjusting at least one of a number of acquisition phases to use for the multi-phase contrast scan and an acquisition timing parameter of the multi-phase contrast scan, based on the measured contrast signal; and performing the multi-phase contrast scan with the imaging system according to the updated scan prescription. In a first example of the method, the pre-determined scan prescription includes a maximum number of acquisition phases for the multi-phase contrast scan and the acquisition timing parameter set to a minimum amount of time, and generating the updated scan prescription for performing the multi-phase contrast scan of the subject based on the measured contrast signal comprises: determining a hemodynamic marker of the subject based on the measured contrast signal; inputting the hemodynamic marker of the subject into a lookup table that outputs at least one of a trim number for removing acquisition phases from the maximum number of acquisition phases and a maximum amount of time to use for the acquisition timing parameter. In a second example of the method, which optionally includes the first example, at least one of the trim number decreases and the maximum amount of time increases as a value of the hemodynamic marker increases. In a third example of the method, which optionally includes one or both of the first and second examples, the hemodynamic marker is determined based on a peak time of the measured contrast signal, and the measured contrast signal is one of an arterial inflow function curve, a venous outflow function curve, and a tissue uptake curve. In a fourth example of the method, which optionally includes any or all of the first through third examples, the acquisition timing parameter is one of an amount of time between a first of the number of acquisition phases and a last of the number of acquisition phases and an amount of time between each of the number of acquisition phases.

In another representation, a system comprises: an x-ray source that emits a beam of x-rays toward a subject to be imaged; a detector that receives the x-rays attenuated by the subject; a data acquisition system (DAS) operably connected to the detector; and a computer operably connected to the DAS and configured with instructions in non-transitory memory that when executed cause the computer to: set a scan prescription for a multi-phase contrast scan of the subject to be a fallback prescription; process projection data of a monitoring region of interest (ROI) of the subject from the DAS to measure a contrast signal of a contrast agent administered to the subject; determine a hemodynamic marker of the subject based on the contrast signal, the hemodynamic marker used to approximate a duration between an arterial peak of the contrast agent at the monitoring ROI and a venous return to baseline of the contrast agent at the monitoring ROI; update the scan prescription based on the hemodynamic marker of the subject; and perform the multi-phase contrast scan according to the updated scan prescription and not the fallback prescription. In a first example of the system, the multi-phase contrast scan in a multi-phase angiography scan, and wherein the hemodynamic marker is determined immediately prior to or during a first acquisition of the multi-phase angiography scan. In a second example of the system, which optionally includes the first example, the fallback prescription includes using a maximum number of acquisition phases for the multi-phase contrast scan with a minimum amount of time between each acquisition phase, and the non-transitory memory stores a lookup table configured to determine at least one of a number of acquisition phases to trim from the maximum number of acquisition phases and an adjusted amount of time between each acquisition phase of the multi-phase contrast scan. In a third example of the system, which optionally includes one or both of the first and second examples, the number of acquisition phases to trim from the maximum number of acquisition phases ranges from zero to a positive non-zero number and the adjusted amount of time between each acquisition phase ranges from the minimum amount of time between each acquisition phase to an amount of time that is greater than the minimum amount of time.

In still another representation, a method for a computing device communicatively coupled to an imaging system comprises: displaying an adaptive scan protocol graphical user interface (GUI) on a display device coupled to the computing device; receiving a multi-phase contrast scan protocol selection via the adaptive scan protocol GUI; adjusting one or more acquisition phase and timing parameters of the selected multi-phase contrast scan protocol in response to user input to the adaptive scan protocol GUI; updating a visual representation of the selected multi-phase contrast scan protocol displayed via the adaptive scan protocol GUI in correspondence to the adjustment of the one or more acquisition phase and timing parameters of the selected multi-phase contrast scan protocol; and storing the adjusted multi-phase contrast scan protocol in a memory of the computing device. In a first example of the method, adjusting one or more acquisition phase and timing parameters of the selected multi-phase contrast scan protocol comprises adjusting a number of acquisition phases of the selected multi-phase scan protocol and/or a timing between each of the number of acquisition phases of the selected multi-phase scan protocol in response to user input to the adaptive scan protocol GUI. In a second example of the method, which optionally includes the first example, adjusting the number of acquisition phases of the selected multi-phase scan protocol and/or the timing between each acquisition phase of the selected multi-phase scan protocol in response to the user input to the adaptive scan protocol GUI comprises: displaying, via the adaptive scan protocol GUI, at least one of an input maximum number of acquisition phases and an input minimum number of acquisition phases for the selected multi-phase scan protocol; displaying, via the adaptive scan protocol GUI, at least one of an input maximum timing between each acquisition phase of the selected multi-phase contrast scan protocol and an input minimum timing between each acquisition phase of the selected multi-phase contrast scan protocol; and adjusting a scan prescription lookup table displayed via the adaptive scan protocol GUI, the scan prescription lookup table including a plurality of rows, based on the input maximum number of acquisition phases, the input minimum number of acquisition phases, the input maximum timing, and the input minimum timing, each row of the plurality of rows defining a set number of acquisition phases and a set timing between each acquisition phase for a timing range of a patient-specific input. In a third example of the method, which optionally includes one or both of the first and second examples, for each row of the plurality of rows of the scan prescription lookup table, the set number of acquisition phases is less than or equal to the input maximum number of acquisition phases and greater than or equal to input minimum number of acquisition phases, and the set timing between each acquisition phase is less than or equal to the input maximum timing and greater than or equal to the input minimum timing. In a fourth example of the method, which optionally includes any or all of the first through third examples, the patient-specific input is selected via a drop-down menu including a plurality of possible patient-specific inputs, the plurality of possible patient-specific inputs including an estimated or measured arterial peak time of an arterial inflow function curve and a first acquisition phase trigger time. In a fifth example of the method, which optionally includes any or all of the first through fourth examples, adjusting one or more acquisition phase and timing parameters of the selected multi-phase contrast scan protocol in response to the user input to the adaptive scan protocol GUI further comprises: displaying, via the adaptive scan protocol GUI, an adjustable time parameter for the timing range of the patient-specific input in at least one row of the scan prescription lookup table; and adjusting the timing range of the patient-specific input in the at least one row and a subsequent row of the scan prescription lookup table in response to user input to the adjustable time parameter. A sixth example of the method, which optionally includes any or all of the first through fifth examples, further comprises: displaying, on the display device, a run-time GUI in response to a request to execute the adjusted multi-phase contrast scan protocol, the run-time GUI including a visual representation of a scan prescription. A seventh example of the method, which optionally includes any or all of the first through sixth examples, further comprises: determining a value of the patient-specific input via a contrast signal measured at a monitoring region of interest (ROI) of a patient; and setting the scan prescription for the imaging system based on the adjusted multi-phase contrast scan protocol and the value of the patient-specific input. In an eighth example of the method, which optionally includes any or all of the first through seventh examples, setting the scan prescription for the imaging system based on the adjusted multi-phase contrast scan protocol and the value of the patient-specific input comprises: setting a prescribed number of acquisition phases and a prescribed timing between each acquisition phase according to the set number of acquisition phases and the set timing between each acquisition phase for the timing range corresponding to the value of the patient-specific input. A ninth example of the method, which optionally includes any or all of the first through eighth examples, further comprises: performing a personalized multi-phase contrast scan of the patient by acquiring the prescribed number of acquisition phases with the prescribed timing between each acquisition phase; and displaying a visual representation of a progress of the personalized multi-phase contrast scan of the patient via the run-time GUI.

In another representation, a method for a computing device communicatively coupled to an imaging system comprises: setting a scan prescription for imaging a patient with the imaging system based on a pre-determined scan protocol and a contrast signal measured from the patient; displaying, on a display device coupled to the computing device, a run-time graphical user interface (GUI), the run-time GUI including a visual representation of the scan prescription; and performing a plurality of acquisition phases with the imaging system according to the scan prescription. In a first example of the method, the visual representation of the scan prescription comprises an adaptive scan prescription section and a scan range selection section. In a second example of the method, which optionally includes the first example, the adaptive scan prescription section comprises a plurality of plurality of user interface control inputs for adjusting, via user input, one or more of a maximum number of acquisition phases for the plurality of acquisition phases, a minimum number of acquisition phases for the plurality of acquisition phases, a minimum amount of time between each phase of the plurality of acquisition phases, and a maximum amount of time between each of phase of the plurality of acquisition phases. In a third example of the method, which optionally includes one or both of the first and second examples, the adaptive scan prescription section displays scan parameters defined via user input to an adaptive scan protocol GUI at a time that is not concurrent with imaging the patient with the imaging system. In a fourth example of the method, which optionally includes any or all of the first through third examples, the scan range selection section displays location markers of a scan range overlaid on scout images of the patient, and the location markers are adjustable via user input to the run-time GUI.

In another representation, a system comprises: a display device; a non-transitory memory storing instructions; and a processor configured to execute the instructions to: display, on the display device, an adaptive scan protocol graphical user interface (GUI); receive a selection of a scan protocol via user input to the adaptive scan protocol GUI; adjust one or more acquisition phase and timing parameters of the scan protocol in response to user input to the adaptive scan protocol GUI; update a visual representation of a scan prescription lookup table displayed via the adaptive scan protocol GUI in correspondence to the adjustment of the one or more acquisition phase and timing parameters of the scan protocol; store the adjusted scan protocol in the non-transitory memory; display, on the display device, a run-time GUI including a visual representation of a personalized scan prescription generated based on the adjusted scan protocol and a hemodynamic marker determined from a contrast signal measured from a patient; and command an imaging system to perform a plurality of acquisition phases according to the personalized scan prescription. In a first example of the system, the scan prescription lookup table includes a plurality of rows, each row defining a number of acquisition phases and a timing between each acquisition phase to include in the personalized scan prescription when the hemodynamic marker of the patient is within a corresponding range defined by the row. In a second example of the system, which optionally includes the first example, the hemodynamic marker used to approximate a duration between an arterial peak of the contrast signal measured from the patient and a venous return to baseline of the contrast signal measured from the patient. In a third example of the system, which optionally includes one or both of the first and second examples, the one or more acquisition phase and timing parameters of the adjusted scan protocol are further adjustable via user input to the run-time GUI. In a fourth example of the system, which optionally includes any or all of the first through fourth examples, the personalized scan prescription is for a multi-phase angiography scan, and wherein the hemodynamic marker is determined immediately before or during a first acquisition phase of the plurality of acquisition phases.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A method, comprising:
    processing acquired projection data of a monitoring area of a subject to measure a contrast signal of a contrast agent delivered to the subject;
    determining a hemodynamic marker of the subject based on the contrast signal;
    generating a scan prescription for a multi-phase contrast scan based on the determined hemodynamic marker of the subject, including determining at least one of a number of acquisition phases to use for the multi-phase contrast scan and an acquisition timing parameter of the multi-phase contrast scan, based on the determined hemodynamic marker of the subject; and
    performing the multi-phase contrast scan according to the scan prescription.

2. The method of claim 1, wherein the monitoring area is an artery and the contrast signal comprises at least a segment of an arterial inflow function (AIF) curve.

3. The method of claim 2, wherein the hemodynamic marker is a peak time of the AIF curve.

4. The method of claim 2, wherein the hemodynamic marker is a venous return to baseline time that is estimated from a peak time of the AIF curve.

5. The method of claim 1, wherein the monitoring area is a tissue of interest, the contrast signal comprises at least a segment of a tissue update curve (TUC), and the hemodynamic marker is a function of a peak time of the TUC.

6. The method of claim 1, wherein generating the scan prescription based on the determined hemodynamic marker of the subject comprises determining at least one of the number of acquisition phases to use for the multi-phase contrast scan and the acquisition timing parameter of the multi-phase contrast scan via a plurality of pre-determined ranges that each relate a value to use for the at least one of the number of acquisition phases to use for the multi-phase contrast scan and the acquisition timing parameter of the multi-phase contrast scan when the determined hemodynamic marker is within a corresponding pre-determined range of the plurality of pre-determined ranges.

7. The method of claim 6, wherein the plurality of pre-determined ranges are included in a lookup table, and determining the at least one of the number of acquisition phases to use for the multi-phase contrast scan and the acquisition timing parameter of the multi-phase contrast scan via the plurality of pre-determined ranges comprises inputting the determined hemodynamic marker of the subject into the lookup table.

8. The method of claim 6, wherein performing the multi-phase contrast scan according to the scan prescription comprises acquiring projection data at a timing based on the acquisition timing parameter defined by the scan prescription for the number of acquisition phases defined by the scan prescription.

9. The method of claim 1, wherein the contrast agent delivered to the subject is one of a timing bolus injection administered prior to performing the multi-phase contrast scan and a contrast agent bolus injection administered for performing the multi-phase contrast scan.

10. A method for an imaging system, comprising:
    processing acquired projection data of a monitoring area of a subject to measure a contrast signal of a contrast agent delivered to the subject via injection;
    generating a scan prescription for a contrast scan of the subject, including determining at least one of a number of acquisition phases to use for the contrast scan and an acquisition timing parameter of the contrast scan, based on the measured contrast signal; and
    performing the contrast scan with the imaging system according to the scan prescription.

11. The method of claim 10, wherein generating the scan prescription for the contrast scan of the subject based on the measured contrast signal comprises:
    determining a hemodynamic marker of the subject based on the measured contrast signal; and inputting the hemodynamic marker of the subject into a lookup table that outputs at least one of the number of acquisition phases to use for the contrast scan and the acquisition timing parameter of the contrast scan for the input hemodynamic marker.

12. The method of claim 11, wherein the hemodynamic marker is determined based on a peak time of the measured contrast signal, and the measured contrast signal is one of an arterial inflow function curve, a venous outflow function curve, and a tissue uptake curve.

13. The method of claim 11, wherein at least one of the number of acquisition phases to use for the contrast scan and the acquisition timing parameter of the contrast scan increases as a value of the hemodynamic maker increases.

14. The method of claim 10, wherein the acquisition timing parameter includes at least one of an amount of time between a first of the number of acquisition phases and a last of the number of acquisition phases and an amount of time between each of the number of acquisition phases.

* * * * *